United States Patent [19]

Robinson

[11] Patent Number: 5,589,372
[45] Date of Patent: Dec. 31, 1996

[54] SQUALENE SYNTHETASE

[75] Inventor: Gordon W. Robinson, Lawrenceville, N.J.

[73] Assignee: E. R. Squibb & Sons, Inc., Princeton, N.J.

[21] Appl. No.: 351,981

[22] Filed: Dec. 8, 1994

Related U.S. Application Data

[63] Continuation of Ser. No. 911,835, Jul. 10, 1992, abandoned, which is a continuation-in-part of Ser. No. 588,235, Sep. 26, 1990, abandoned.

[51] Int. Cl.⁶ .............................. C12N 1/21; C12N 5/10; C12N 15/54; C12N 15/63
[52] U.S. Cl. .................. 435/193; 435/240.2; 435/252.3; 435/254.11; 435/320.1; 536/23.2; 536/24.3
[58] Field of Search ...................... 536/23.2; 435/320.1, 435/240.2, 252.3, 254.2, 193

[56] References Cited

U.S. PATENT DOCUMENTS 5,032,519  7/1991  Paulson et al. .................... 435/193

OTHER PUBLICATIONS

Sambrook et al., Molecular Cloning, A Laboratory Manual, Cold Spring Harbor Lab. Press, 1989, pp. 11–3 to 11–19.
Brock, T. D. et al.; *Biology of Microorganisms*, Fourth Edition, Prentice–Hall Inc., Englewood Cliffs, NJ, 1984, pp. 59, 686–687.
Hanley, K. et al.; Plant Physiol. 98:215–220 (1992).
Belingheri, L. et al.; FEBS Lett. 292:34–36 (1991).
Jennings, S. M. et al.; Proc. Natl. Acad. Sci. USA 88:6038–6042 (Jul. 15, 1991).
Fegueur, M. et al.; Curr. Genet. 20:365–372 (1991).
Händler, B. et al.; Abstr. 201st Natl. Mtg. Amer. Chem. Soc., Part I, Biot. Abstr. #92 (Apr. 1991).
Robinson, G. W. et al; Circulation, vol. 82, Suppl. III:610 (1990).
Haffey, M. L. et al.; J. Virol. 62:4493 (1988).
Faust, J. R. et al.; Proc. Natl. Acad. Sci. USA 76:5018–5022 (1979).
Grimm, C. et al.; Mol. Gen. Genet. 215:81–86 (1988).
Shechter, I. et al.; J. Biol. Chem. 267:8628–8635 (1992).

*Primary Examiner*—Robert A. Wax
*Assistant Examiner*—Eric Grimes
*Attorney, Agent, or Firm*—Thomas R. Savitsky; Timothy J. Gaul; James M. Bogden

[57] ABSTRACT

Nucleic acid sequences, particularly DNA sequences, coding for all or part of a squalene synthetase, expression vectors containing the DNA sequences, host cells containing the expression vectors, and methods utilizing these materials. The invention also concerns polypeptide molecules comprising all or part of a squalene synthetase, and methods for producing these polypeptide molecules.

20 Claims, 12 Drawing Sheets

FIG. 2A

```
TCTAGAGACCCTGCGAGCCGTGTCCCGGTGGGTTCTGGGAGCTCTAACTCCGCAGAACTACAAACCTTGCTTACACAGA         79
Xba1
GTGAACCTGCTGCCTGGCGTGCCTGACTCAGTACATTCATAGCCCATCTTCAACAACAATACCGACTTACCATCCTA         158

TTTGCTTTGCCCTTTTCTTTCCACTTGCATCGGAAGGCGTTATCGGTTTGGGTTTAGTGCCTAAACGAGC              237

AGCCGAGAACACGACCACGGG TATATAAA TGAAAGTTAGGACACAGGGGCAAAGAATAAGAGCACAGAAGAGAGAAAG      316

ACGAAGAGCAGAAGCGGAAAAC GTATAC ACGTCACATATCACACACAACAATGGGAAAGCTATTACAATTGGCATTGC      395
                         Acc1                        M  G  K  L  L  Q  L  A  L         9

ATCCGGTCGAGATGAAGGCAGCTTTGAAGCTTTGAAGCTTTGCAGAACACCGCTATTCTCCATCTATGATCAGTCCACGTC     474
 H  P  V  E  M  K  A  A  L  K  L  K  F  C  R  T  P  L  F  S  I  Y  D  Q  S  T  S       36

TCCATATCTCTGCACTGTTTCGAACTGTTGACCTCCAGATCGTTGCTGTGATCAGAGAGCTGCATCCA              553
 P  Y  L  H  C  F  E  L  L  [N] L  T  S  R  S  F  A  A  V  I  R  E  L  H  P            62

GAATTGAGAAACTGTGTTACTCTCTTTTATTTAAGGGCTTGGATACCATCGAAGACGATATGTCCATCGAAC          632
 E  L  R  N  C  V  T  L  F  Y  L  I  L  R  A  L  D  T  I  E  D  D  M  S  I  E           88

ACGATTGAAAATTGACTTGTTGCGTCACTTCCACGAGAAATTGTTGTTAACTAAATGGAGTTTCGACGGAAATGCCCC    711
 H  D  L  K  I  D  L  L  R  H  F  H  E  K  L  L  T  K  W  S  F  D  G  N  A  P         115
                                                  EcoR1
CGATGTGAAGGACAGAGCCGTTTTGACAGATTTCGAATCGATTCTTATTGAATTC CACAAATTGAAACCAGAATATCAA     790
 D  V  K  D  R  A  V  L  T  D  F  E  S  I  L  I  E  F  H  K  L  K  P  E  Y  Q         141

GAAGTCATCAAGGAGATCACCGAGAAAATGGGTAATGGCCGACTACATCTTGATGAAATTACAACTTGAATG            869
 E  V  I  K  E  I  T  E  K  M  G  N  G  M  A  D  Y  I  L  D  E  N  Y  N  L  N         167

GGTTGCAAACCGTCCACGACTACGACGTCCACTGTCCACTACGTCCACGTGTTTGGTGCGTGATGGTTTGACCCGTTTGAT  948
 G  L  Q  T  V  H  D  Y  D  V  Y  C  H  Y  V  A  G  L  V  G  D  G  L  T  R  L  I      194

TGTCATTGCCAAGTTTGCCAACATCTTTGTATTCTAATGAGCAATTGTATGAAAGCATGGTTTCCTACAAAAA           1027
 V  I  A  K  F  A  [N] E  S  L  Y  S  N  E  Q  L  Y  E  S  M  G  L  F  L  Q  K        220
```

```
ACCAACATCATCAGAGACTACAATGAAGATTGGTCGATGGTAGATCCTTCTGGCCCAAGGAAATCTGGTCACAATACG   1106
 T  N  I  I  R  D  Y  N  E  D  L  V  D  G  R  S  F  W  P  K  E  I  W  S  Q  Y     246

CTCCCAGTTGAAGGACTTCATGAAACCTGAAAACGAACAACTGGGGTTGGACTGTATAAACCACCTCGTCTTAAACGC   1185
 A  P  Q  L  K  D  F  M  K  P  E  N  E  Q  L  G  L  D  C  I  N  H  L  V  L  N  A  273

ATTGAGTCATGTTATCGATGTTGTTGACTTATTGGGCCAGTATCCCACGAGCAATCCACTTTCCAATTTTGTGCCATTCCC 1264
 L  S  H  V  I  D  V  L  T  Y  L  A  S  I  H  E  Q  S  T  F  Q  E  C  A  I  P     299

CAAGTTATGGCCATTGCAACCTTGGCTTGGTATTCAACAACCGTGAAGTGCTACACCGTGAAGATTCGTAAGG        1343
 Q  V  M  A  I  A  T  L  A  L  V  F  N  N  R  E  V  L  H  G  N  V  K  I  R  K     325

GTACTACCTGCTATTTAATTTGAAATCAAGGACTTTGCGTGTGGCTGTGTCGAGATTTTGACTATTACGTGATAT      1422
 G  T  T  C  Y  L  I  L  K  S  R  T  L  R  G  C  V  E  I  F  D  Y  Y  L  R  D  I  352

CAAATCTAAATTGGCTGTGCAAGATCCAAATTTCTTAAAATTGAACATTCAAATCTCCAAGATCGAACAATTCATGAA    1501
 K  S  K  L  A  V  Q  D  D  P  N  F  L  K  L  N  I  Q  I  S  K  I  E  Q  F  M  E   378

GAAATGTACCAGGATAATTACCTCCTAACGTGAAGCCAAATGAAACTCCAATTTCTTGAAAGTTAAAGAAAGATCCA    1580
 E  M  Y  Q  D  K  L  P  P  N  V  K  P  N  E  T  P  I  F  L  K  V  K  E  R  S     404

GATACGATGATGAATTGGTCCCAACCAAGAAGAGTACAAGTTCAATATGGTTTTATCTATCATCTTGTCCGT         1659
 R  Y  D  D  E  L  V  P  T  Q  Q  E  E  E  Y  K  E  N  M  V  L  S  I  I  L  S  V  431

TCTTCTTGGGTTTTATTATATACACTTTACACAGAGCGTGAAGTCTGCGCCAAATAACAAACATAAACAACTCCGAA    1738
 L  L  G  F  Y  Y  I  Y  T  L  H  R  A  *                                         444

CAATAACTAAGTACTTACATAATAGGTAGAGGCCTATCCTTAAAGATAACCTTATATTTCATTACATCAACTAATTCGA  1817

CCTTATTATCTTCGAATTGAAATGCATTATACCGTCGTTAGCTTTGTCACCTTCCCAGTAAACGTTGTTT          1896

CTTGCCGACAAACAATGTGGCCCTCTCCGTCAATCTGTAACGACCCAAATCGTATTAAAGTTTCGCCGTCCTGTTCA    1975

CTGAACCTTCCCTCATTGGAGAATCTCTCCGCCAGGACGCAAAGTCCTTAGGCAACTCTAGTTCACCTTGAATCT      2054
```

FIG. 2B

```
CTAAAGGCGTTTATATAATGAGTTTAGCTAACCGCATTGAAGAAATCCGGTGCCTTTGTCAGTACAAGCTTTGGAATGACCTTCCTTCTTATGGAGAA    99
                M  S  L  A  N  R  I  E  E  I  R  C  L  C  Q  Y  K  L  W  N  D  L  P  S  Y  G  E      27

GACGAAAATGTGCCTCAAAACATCCGCCGTTGTTACCAATTACTCGATATGACCTCGAGTCGTTGCAGTCGTTAAAGATTGCCAAATGGTATT        198
 D  E  N  V  P  Q  N  I  R  R  C  Y  Q  L  L  D  M  T  S  R  S  F  A  V  V  I  K  Q  L  P  N  G  I    60

AGAGAGGCTGTTATGATTTTTATCTTGTCCTTCGTGGACTGGATACAGTAGAGGATGACATGACGTTGCCTTTGGATAAAAAGCTTCCAATCCTAAGA    297
 R  Q  A  V  M  I  F  F  Y  L  V  L  R  G  L  D  T  V  E  D  D  M  T  L  P  L  D  K  K  L  P  I  L  R  93

GATTTTTATAAAACAATTGAAGTCGAAGGGTGGACGTTTAATGAATCTGGTCCTAACGAAAAGGATCGTCAGCTTCTCGTAGAATTCGACGTGGTATA    396
 D  F  Y  K  T  I  E  V  E  G  W  T  F  N  E  S  G  P  N  E  K  D  R  Q  L  L  V  E  F  D  V  V  I   126

AAAGATATCTTAACCTGTCAGAGAGGTTATCGTAATGTATTCGAACATTACTAAGGAAATGGGTGATGGTATGGCTTATTATGCCTCTCTTGCCGAA    495
 K  E  Y  L  N  L  S  E  G  Y  R  N  V  I  S  N  I  T  K  E  M  G  D  G  M  A  Y  Y  A  S  L  A  E   159

AAAAATGACGGATTCTCTGTAGAAACTATAGAAGACTTTAACAAATATTGTCATTATGTTGCCGGATTGGTGGGAATTGGTGGATTCTCGTTTGCT    594
 K  N  D  G  F  S  V  E  T  I  E  D  F  N  K  Y  C  H  Y  V  A  G  L  V  G  I  G  L  S  R  L  F  A   192

CAATCTAAGCTAGAAGATCCGGATTTAGCTCATAGTCAAGCTATTTCCAATTCTCTTGGACTCTTTTTACAAAAAGTAACATCATTCGTGATTATCGT    693
 Q  S  K  L  E  D  P  D  L  A  H  S  Q  A  I  S  N  S  L  G  L  F  L  Q  K  V  N  I  I  R  D  Y  R   225

GAGGATTTTGATGATAATCGTCATTTCTGGCCCTCGTGAAATTTGGTCAAGTACTTCCAGTTTCGGTGATCTCTGTTTATCTTCAATTGAAGACTCAGGAAATATTTAAT    792
 E  D  F  D  D  N  R  H  F  W  P  R  E  I  W  S  K  Y  T  S  S  F  G  D  L  C  L  P  D  N  S  E  K   258

GCTCTTGAATGTTTATCTGATATGACTGCTAATGCTGCCACATTAGCTGCAGTTTTCAGAAACCCGGATGTTTTCAACTAATGTTAAGGAAGGGTCAG    891
 A  L  E  C  L  S  D  M  T  A  N  A  A  T  L  A  A  V  F  R  N  P  D  V  F  Q  T  N  V  K  I  R  K  G  Q 291

TTCTGTGCTATTCCACAAGTAATTCTACATTCTGTAAACTTGAAGATGTTGTGTGATTTATTCCTTCGTTACACCCGTCGTGATATTCATTATAAGAACACTCCTAAGGAT    990
 F  C  A  I  P  Q  V  I  L  H  S  V  N  L  F  F  L  R  Y  T  R  D  I  H  Y  K  N  T  P  K  D   324

GCTGTCCAGATTATTCTACATTCTGTAAACTTGAATGTGAGCAAGTATCTGAAAGTATCTGAAAGCTTATTTCCTCCGTGAGATGTACGAAAGGCCTAT    1089
 A  V  Q  I  I  L  H  S  V  N  L  K  N  V  C  D  L  F  F  L  R  Y  S  E  S  L  F  P  R  R  F  R  E  M  Y  E  K  A  Y 357

CCCAACTTTTGAAGATTTCAATGAAGATTGTGAACAAGATTGAGCAAGTATGAAAGTATCTGAAAAGCAATTTAAATGACGAGCAAAAGGAATTGTATCGAAAGGATTTACAGAAACTA  1188
 P  N  F  L  K  I  S  I  E  C  G  K  I  K  K  G  N  G  T  Q  K  A  I  L  N  D  E  Q  K  E  L  Y  R  K  D  L  Q  K  L  390

GTTAGTAAGTTGTCTGAACAAAAAGAAGGGAAACTCAGAAGGCAATTTAAATGACGAGCAAAAGGAATTGTATCGAAAGGATTTACAGAAACTA    1287
 V  S  K  L  S  E  Q  K  K  G  N  G  T  Q  K  A  I  L  N  D  E  Q  K  E  L  Y  R  K  D  L  Q  K  L   422

GGCATTAGCATTCTTTTGTATTTTTATAATCCTTGTCATTTCTGTATGCCTTGTCATTTCTGTATGCCTTGCTTGTGTTCAATATTAGAATACAAGCAGTTTAAAAAAAAAAAAACTA    1386
 G  I  S  I  L  F  V  F  F  I  I  L  V  C  L  A  V  I  F  Y  V  F  N  I  R  I  H  W  S  D  F  K  E  456

CTTAATTTGTTTAGTCCGTAAATTTAAAAAAACTTAAATACTGGTTCAATATCGATAATATACAAGCAGTTTAAAAAAAAAAAAACTTT    1479
 L  N  L  F  *                                                                                        460
```

FIG. 8

```
TGCGCCAGGATGGAGTTCGTGAAATGCCTTGGCCACCCGAAGAGTTCTACAACCTGGTGCGCTTCCGGATCGGGGGCAAGGGAAGGTGATGCCAAG    99
 M  E  F  V  K  C  L  G  H  P  E  E  F  Y  N  L  V  R  F  R  I  G  G  K  R  K  V  M  P  K            30

ATGGACCAGGACTCGCTCAGCAGCAGCCTGAAAACTTGCTACAAGTATCTCAATCAGACTCGCAGTTTCGCAGTTGATCCAGGCGCTGGATGGG    198
 M  D  Q  D  S  L  S  S  S  L  K  T  C  Y  K  Y  L  N  Q  T  S  R  S  F  A  A  V  I  Q  A  L  D  G  63

GAAATGCGCAACGCAGTGTGCATATTTTATCTGGTTCTCCGAGCTCTGGAAGATGACACACTGGAAGATGACATGACCATCAGTGTGGAAAAGAAGGTCCCGCTG    297
 E  M  R  N  A  V  C  I  F  Y  L  V  L  R  A  L  E  D  D  M  T  I  S  V  E  K  K  V  P  L            96

TTACACAACTTTCACTCTTTCCTTTACCAACCAGACTGGCCGGGTTTACCAGCCGGACTGGAGGTTCATGGAGAGCAAGGAAGGATGCTCCAACGATCTCC    396
 L  H  N  F  H  S  F  L  Y  Q  P  D  W  R  F  M  E  S  K  E  K  D  R  Q  V  L  E  D  F  P  T  I  S    129

CTTGAGTTTAGAAATCTGGCTGAGAAATACCAAACAGTGATTGCCGACATTTGCCGGAGAATGGGCATTGGGATGGCAGAGTTTTGGATAAGCATGTG    495
 L  E  F  R  N  L  A  E  K  Y  Q  T  V  I  A  D  I  C  R  R  M  G  I  G  M  A  E  F  L  D  K  H  V   162

ACCTCTGAACAGGAGTGGGACAAGTACTGCCACTATGTTGCTGGGCTGGTTCTCTTTCTCAGCCTCAGAGTTTCAGCCTCAGCAAGTGAAGACCCC    594
 T  S  E  Q  E  W  D  K  Y  C  H  Y  V  A  G  L  V  L  F  L  S  R  L  F  S  A  S  E  F  F  E  D  P   195

TTAGTTGGTGAAGATACAGAAGAACGTGCCAACTCTATGGGCCTGTTTCTGCAGAAAAACATCATCCGTGACTATCTGGAAGACCAGCAGGGGAGA    693
 L  V  G  E  D  T  E  R  A  N  S  M  G  L  F  L  Q  K  N  I  I  R  D  Y  L  E  D  Q  Q  G  G  R     228

GAGTTCTGGCCTCAAGAGGTTTGGAGCAGGTATGTGTTAAGAAGTTCATCACCTACCTTGTGTTAACTTCTGCGCTATTCCACAGGTG            792
 E  F  W  P  Q  E  V  W  S  R  Y  V  K  K  L  G  D  F  A  K  P  E  N  I  D  L  A  V  Q  C  L  N  E   261

CTTATAACCAATGCCACTGCACCAGACTTTGGCTGCCTGTTTATATAACCAGGAGACTGTCAAAGGGCAGTGAAGATTCATAGAATCCCGACTCAGACCCATCTTCTAGCAAACAAGG    891
 L  I  T  N  A  L  H  H  I  P  D  V  I  T  Y  L  S  R  L  R  N  Q  S  V  F  N  F  C  A  I  I  P  Q  V  294

ATGGCCATTGCCACTTTGGCTGTCAAAGCCATCGATTTCAAGGGCGCAGTGAAGATTTATCATGAAGAGATTTATCAGTATGAAGGGCAGTGTTCAAAGGGCCAGGCAGTGACCCTGATGATGGAT    990
 M  A  I  A  T  L  A  A  V  K  A  I  D  F  K  G  A  V  K  I  Y  H  R  I  P  D  S  D  P  S  S  K  T  R  327

GCCACCAATATGCCAGCTGTCAAAGCCATCGATTTCAAGGGCGCAGTGAAGATTTATCATAGAATCCCCGACTCAGACCCATCTTCTAGCAAACAAGG   1089
 A  T  N  M  P  A  V  K  A  I  D  F  K  G  A  V  K  I  Y  H  R  I  P  D  S  D  P  S  S  K  T  R      360

CAGATCATCTCCACCATCCGGACGTGTACCTGACTCTCTCTCCAGGTAACAGAGAAGACTTCCCCGAAGCCACTACTCCCCATCTACCTGTCTGTTTGTCATGCTTTG   1188
 Q  I  I  S  T  I  R  T  Q  N  L  P  N  C  Q  L  I  S  R  S  H  Y  S  P  I  Y  L  S  F  V  M  L  L    393

GCTGCCCTGAGCTGCCAGTGGCAGTACCTGACTGAGACGACTGAACAGAAGACTATGCAGATTCAGAGACTGATCCCCAAATTTGTCCATAGCTGAAG   1287
 A  L  S  W  Q  Y  L  T  T  L  S  Q  V  T  E  D  Y  V  Q  T  G  E  H  *                               417

TCCACCATAAAGTGGATTTACTTTTTTTTCTTTAAAAAAAAAAAAAAAAAAAAAAAAAAAA                                        1349
```

FIG. 9

```
Hs.ERG9  MEFVKCLGHP EEFYNLVRFR IGGKRKVMPK MDQDSLSSSL KTCYKYLNQT   50
Sc.ERG9  MGKLLQL-AL HPVEMKAALK LKFCRTPLFS IYDQSTSPYL LHCFELLNLT   49
Sp.ERG9  MS--LAN-RI EEIRCLCQYK L-WNDLPSYG -EDENVPQNI RRCYQLLDMT   45

Hs.ERG9  SRSFAAVIQA EDGEMRNAVC IFYLVLRALD TLEDDMTISV EKKVPLLHNF  100
Sc.ERG9  SRSFAAVIRE LHPELRNCVT LFYLILRALD TIEDDMSIEH DLKIDLLRHF   99
Sp.ERG9  SRSFAVVIKQ LPNGIRQAVM IFYLVLRGLD TVEDDMLPL DKKLPILRDF   95

Hs.ERG9  HSFLYQPDWR FMES--KEKD RQVLEDFPTI SLEFRNLAEK YQTVIADICR  148
Sc.ERG9  HEKLLLTKWS FDGNAPDVKD RAVLTDFEST LIEFHKLKPE YQEVIKETTE  149
Sp.ERG9  YKTIEVEGWT FNESGPNEKD RQLLVEFDVV IKEYLNLSEG YRNVISNITK  145

Hs.ERG9  RMGIGMAEF- -LDKH----- VTSEQEWDKY CHYVAGLVGI GLSRLFSASE  191
Sc.ERG9  KMGNGMADY- ILDENYNLNG LQTVHDYDVY CHYVAGLVGD GLTRLIVIAK  198
Sp.ERG9  EMGDGMAYYA SLAEKNDGFS VETIEDFNKY CHYVAGLVGI GLSRLFAQSK  195

Hs.ERG9  FEDPLVGEDT ERANSMGLFL QKINIIRDYL EDQQGGREFW PQEVWSRYVK  241
Sc.ERG9  FANESLYSNE QLYESMGLFL QKINIIRDYN EDLVDGRSFW PKEIWSQYAP  248
Sp.ERG9  LEDPDLAHSQ AISNSLGLFL QKVNIIRDYR EDFDDNRHEW PREIWSKYTS  245

Hs.ERG9  KLGDFAKPEN IDLAVQCLNE LITNALHHIP DVITYLSRLR NQSVFNFCAI  291
Sc.ERG9  QLKDFMKPEN EQLGLDCINH LVINALSHVI DVLTYLASIH EQSTFQFCAI  298
Sp.ERG9  SFGDLCIPDN SEKALELSD MTANALTHAT DALVYLSQLK TQEIFNFCAI  295

Hs.ERG9  PQVMAIATLA ACYNNQQVFK GAVKIRKGQA VTLMMDATNM PAVKAI----  337
Sc.ERG9  PQVMAIATLA LVFNNREVLH GNVKIRKGTT CYLILKSRTL RGCVEIFDYY  348
Sp.ERG9  PQVMAIATLA AVFRNPDVFQ TNVKIRKGQA VQIILHSVNL KNVCDLFLRY  345

Hs.ERG9  ---------- ---------- ----IYQYME EIYHRIPDSD PSSSKTRQII  363
Sc.ERG9  LRDIKSKLAV QDPNFLKLNI QISKIEQFME EMYQDKLPPN VKPNETPIFL  398
Sp.ERG9  TRDIHYKNTP KDPNFLKISI ECGKIEQVSE SLFPRRFREM YEKAYVSKLS  395

Hs.ERG9  STIRTQ--NL PNCQLISRSH YSPIYLSFVM LLAALSWQYL TTLSQVTEDY  411
Sc.ERG9  KVK-----ER SRYDDELVPT QQEEEYKFNM VLSIILSVLL GFYYIYTLHR  443
Sp.ERG9  EQKKGNGTQK AILNDEQKEL YRKDLQKLGI SILFVFFIIL VCLAVIFYVF  445

Hs.ERG9  VQTGEH---- -----                                       417
Sc.ERG9  A--------- -----                                       444
Sp.ERG9  NIRIHWSDFK ELNLF                                       460
```

FIG. 10

SQUALENE SYNTHETASE

This is a continuation of U.S. Ser. No. 07/911,835, filed Jul. 10, 1992, now abandoned, which is a continuation-in-part of U.S. Ser. No. 588,235, filed Sep. 26, 1990, now abandoned.

BACKGROUND OF THE INVENTION

In the mevalonate biosynthetic pathway of most eukaryotes, farnesyl pyrophosphate (FPP) is incorporated into a wide variety of end-products, including dolichols, ubiquinone, hormones, haem A, sterols, and some isoprenylated proteins. Differential synthesis of these FPP-derived products is controlled through both regulated enzyme synthesis and differing affinities for FPP by the multiple enzymes that utilize this substrate. In mammalian cells, the enzymes of non-sterol polyisoprene synthesis possess high affinities for FPP but are synthesized at low constitutive levels. Conversely, squalene synthetase, the first committed enzyme of sterol biosynthesis, has a lower affinity for FPP but levels of this enzyme are regulated; a ten-fold depression in activity is seen in cells when they accumulate sufficient cholesterol. Together, these factors, in concert with regulation of mevalonate production by HMG CoA reductase (HMGR), ensure that adequate non-sterol products of FPP are made both in cells actively synthesizing cholesterol from FPP and in cells that receive most of their cholesterol exogenously, through uptake mediated by the low density lipoprotein (LDL) receptor. An understanding of how, at the molecular level, the cell achieves regulation of squalene synthetase activity is currently lacking.

Characterization of squalene synthetase has lagged behind that of many other enzymes of cholesterol metabolism due to intrinsic problems in working with this microsomal enzyme which, though present in many eukaryotes, is difficult to isolate and stabilize. The enzyme from the yeast *Saccharomyces cerevisiae* has been studied. It is typically solubilized with deoxycholate or nonionic detergents and after further purification, this enzyme is reported to have a monomeric molecular mass estimated at 55,000, 53,000, or 47,000. The solubilized enzyme usually retains the native enzyme's ability to condense two molecules of FPP into squalene in the presence of reduced pyridine nucleotides. Detailed characterization of the enzyme and its active site has been retarded by the poor yields of purified enzyme obtained.

It would be useful to have a source of large amounts of squalene synthetase to expedite its study and characterization.

SUMMARY OF THE INVENTION

The present invention concerns an isolated nucleic acid molecule comprising a nucleic acid sequence coding for all or part of squalene synthetase. Preferably, the nucleic acid molecule is a DNA (deoxyribonucleic acid) molecule, and the nucleic acid sequence is a DNA sequence. Further preferred is a DNA sequence having all or part of the nucleotide sequence substantially as shown in FIGS. 2, 8 or 9. Also preferred is a DNA sequence which has been modified (e.g., disrupted, deleted or truncated) so as to code for a squalene synthetase which is not catalytically active. Additionally preferred is a DNA sequence coding for a modified squalene synthetase in which the carboxy terminal transmembrane sequence has been removed.

The present invention further concerns expression vectors comprising a DNA sequence coding for all or part of squalene synthetase.

The present invention additionally concerns prokaryotic or eukaryotic host cells containing an expression vector which comprises a DNA sequence coding for all or part of squalene synthetase.

The present invention also concerns methods for detecting nucleic acid sequences coding for all or part of squalene synthetase or related nucleic acid sequences.

The present invention further concerns methods for detecting a substrate or inhibitor of squalene synthetase.

The present invention further concerns polypeptide molecules comprising all or part of squalene synthetase. Preferably, the polypeptide molecule is a modified squalene synthetase in which the carboxy terminal transmembrane sequence has been removed.

BRIEF DESCRIPTION OF THE DRAWINGS

FIG. 2 shows the primary nucleotide and amino acid sequence of the squalene synthetase gene of *Saccharomyces cerevisiae*. Two potential N-linked glycosylation sites are underlined with dashed lines. Four potential membrane-spanning domains are underlined and the single "PEST" sequence is double-underlined. In ERG9 5' and 3'-untranslated regions, a consensus TATA transcriptional regulatory element and a possible polyadenylation signal are boxed.

FIG. 8 shows the nucleotide and deduced amino acid sequences of the *Schizosaccharomyces pombe* squalene synthetase.

FIG. 9 shows the nucleotide and deduced amino acid sequences of human squalene synthetase.

FIG. 10 shows a comparison of the amino acid sequences of human (Hs), *Saccharomyces cerevisiae* (Sc) and *Schizosaccharomyces pombe* (Sp) squalene synthetases.

DETAILED DESCRIPTION OF THE INVENTION

Figure 1:
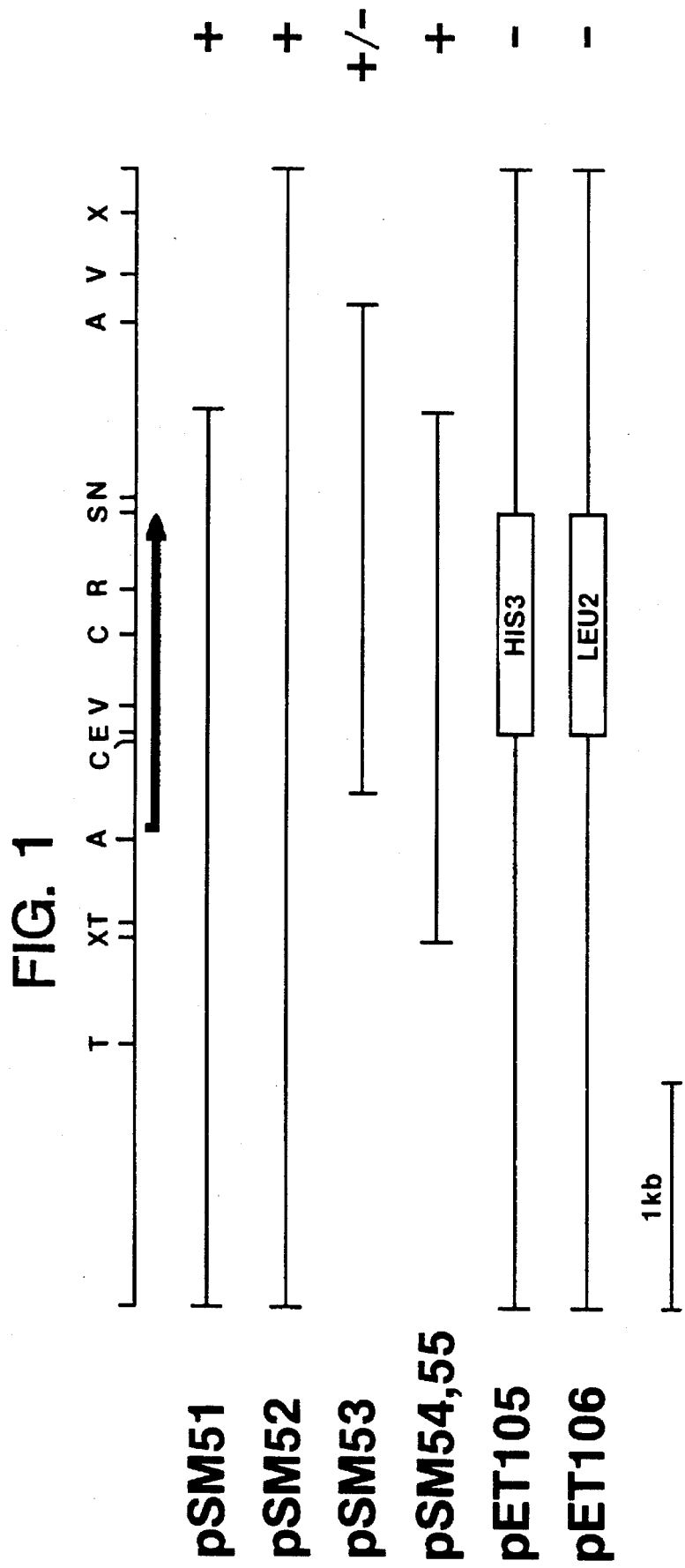
FIG. 1 shows a restriction map of the squalene synthetase (ERG9) chromosomal locus and plasmid subclones. Restriction enzymes: A, Acc1; C, Cla1; E, EcoR1; N, Nsi1; R, EcoR5; S, Sca1; T, Sst1; V, SnaB1; X, Xba1.

The present invention concerns an isolated nucleic acid molecule comprising a nucleic acid sequence coding for all or part of squalene synthetase. Preferably, the nucleic acid molecule is a DNA molecule and the nucleic acid sequence is a DNA sequence. Further preferred is a DNA sequence having all or part of the nucleotide sequence substantially as shown in FIGS. 2, 8 or 9, or a DNA sequence complementary to one of these DNA sequences. Also preferred is a DNA sequence which has been modified (e.g., disrupted, deleted or truncated) so as to code for a squalene synthetase molecule which is not catalytically active. Additionally preferred is a DNA sequence coding for a modified squalene synthetase in which the carboxy terminal transmembrane sequence has been removed. In the case of a nucleotide sequence (e.g., a DNA sequence) coding for part of squalene synthetase, it is preferred that the nucleotide sequence be at least about 15 nucleotides in length.

As used in the present application, the term "squalene synthetase" refers to a polypeptide or protein which is able to catalyze the following reaction: 2 Farnesyl Pyrophospate+NAD(P)H→NAD(P)+Squalene+PPi+H$^+$, where M$^{+2}$ is a co-factor divalent metal cation (Mg$^{+2}$, Mn$^{+2}$). However, the squalene synthetase molecules of the present invention do not necessarily need to be catalytically active. For example, catalytically inactive squalene synthetase or fragments thereof may be useful in raising antibodies to the protein.

As used in the present application, the term "modified", when referring to a nucleotide or polypeptide sequence, means a nucleotide or polypeptide sequence which differs from the wild-type sequence found in nature.

The DNA sequences of the present invention can be isolated from a variety of sources, although the presently preferred sequences have been isolated from yeast/fungal genomic and cDNA and human cDNA libraries. The exact amino acid sequence of the polypeptide molecule produced will vary with the initial DNA sequence.

The DNA sequences of the present invention can be obtained using various methods well-known to those of ordinary skill in the art. At least three alternative principal methods may be employed:

(1) the isolation of a double-stranded DNA sequence from genomic DNA or complementary DNA (cDNA) which contains the sequence;

(2) the chemical synthesis of the DNA sequence; and (3) the synthesis of the DNA sequence by polymerase chain reaction (PCR).

In the first approach, a genomic or cDNA library can be screened in order to identify a DNA sequence coding for all or part of squalene synthetase. For example, a yeast genomic DNA library can be screened in order to identify the DNA sequence coding for all or part of yeast squalene synthetase. Various yeast genomic DNA libraries, for example, the Nasmyth library available from the American Type Culture Collection, Rockville, Md., and the Botstein library available from Dr. D. Botstein (Genentech, Inc., South San Francisco, Calif.) can be employed. Various techniques can be used to screen the genomic DNA or cDNA libraries.

For example, labeled single stranded DNA probe sequences duplicating a sequence present in the target genomic DNA or cDNA coding for all or part of squalene synthetase can be employed in DNA/DNA hybridization procedures carried out on cloned copies of the genomic DNA or cDNA which have been denatured to single stranded form.

A genomic DNA or cDNA library can also be screened for a genomic DNA or cDNA coding for all or part of squalene synthetase using immunoblotting techniques.

In one typical screening method suitable for either immunoblotting or hybridization techniques, the genomic DNA library, which is usually contained in a vector such as λGT11, or cDNA library is first spread out on agarose plates, and then the clones are transferred to filter membranes, for example, nitrocellulose membranes. A DNA probe can then be hybridized or an antibody can then be bound to the clones to identify those clones containing the genomic DNA or cDNA coding for all or part of squalene synthetase.

In the second approach, the DNA sequence of the present invention coding for all or part of squalene synthetase can be chemically synthesized. For example, the DNA sequence coding for squalene synthetase can be synthesized as a series of 100 base oligonucleotides that can then be sequentially ligated (via appropriate terminal restriction sites) so as to form the correct linear sequence of nucleotides.

In the third approach, the DNA sequences of the present invention coding for all or part of squalene synthetase can be synthesized using PCR. Briefly, pairs of synthetic DNA oligonucleotides at least 15 bases in length (PCR primers) that hybridize to opposite strands of the target DNA sequence are used to enzymatically amplify the intervening region of DNA on the target sequence. Repeated cycles of heat denaturation of the template, annealing of the primers and extension of the 3'-termini of the annealed primers with a DNA polymerase results in amplification of the segment defined by the 5' ends of the PCR primers. See, White, T. J. et al., Trends Genet. 5, 185–189 (1989).

The DNA sequences of the present invention can be used in a variety of ways in accordance with the present invention. For example, they can be used as DNA probes to screen other cDNA and genomic DNA libraries so as to select by hybridization other DNA sequences that code for proteins related to squalene synthetase. In addition, the DNA sequences of the present invention coding for all or part of yeast squalene synthetase can be used as DNA probes to screen other cDNA and genomic DNA libraries to select by hybridization DNA sequences that code for squalene synthetase molecules from organisms other than yeast.

The DNA sequences of the present invention coding for all or part of squalene synthetase can also be modified (i.e., mutated) to prepare various mutations. Such mutations may be either degenerate, i.e., the mutation does not change the amino acid sequence encoded by the mutated codon, or non-degenerate, i.e., the mutation changes the amino acid sequence encoded by the mutated codon. These modified DNA sequences may be prepared, for example, by mutating the squalene synthetase DNA sequence so that the mutation results in the deletion, substitution, insertion, inversion or addition of one or more amino acids in the encoded polypeptide using various methods known in the art. For example, the methods of site-directed mutagenesis described in Taylor, J. W. et al., Nucl. Acids Res. 13, 8749–8764 (1985) and Kunkel, J. A., Proc. Natl. Acad. Sci. USA 82, 482–492 (1985) may be employed. In addition, kits for site-directed mutagenesis may be purchased from commercial vendors. For example, a kit for performing site-directed mutagenesis may be purchased from Amersham Corp. (Arlington Heights, Ill.). In addition, disruption, deletion and truncation methods as described in Sayers, J. R. et al., Nucl. Acids Res. 16, 791–800 (1988) may also be employed. Both degenerate and non-degenerate mutations may be advantageous in producing or using the polypeptides of the present invention. For example, these mutations may permit higher levels of production, easier purification, or provide additional restriction endonuclease recognition sites. All such modified DNA and polypeptide molecules are included within the scope of the present invention.

Particularly useful modifications of the DNA sequences of the present invention coding for all or part of squalene synthetase are those in which the coding region of squalene synthetase is modified by disruption or partial replacement of these sequences with those of a marker DNA such as the URA3 gene of yeast or the G418 resistance gene of bacteria. Such modified coding regions preferably contain at least about 200 bp of squalene synthetase flanking sequences both 5' and 3' of the marker insertion site and encode a squalene synthetase that is catalytically inactive. These inactivated squalene synthetase genes can be used to produce chromosomal disruptions or deletions of squalene synthetase by introduction into and subsequent homologous recombination with the DNA of various host cells. For example, they can be used to disrupt the ERG9 gene of yeast by transformation of the appropriate URA3-disrupted DNA into a ura3 mutant cell and selection for URA$^+$ prototrophs using methods described in R. J. Rothstein, Methods Enzymol. 101, 202 (1983). Similar approaches described in Capecchi, M. R., Science 244, 1288–1292 (1989) and Capecchi, M. R., Trends Genet. 5, 70–76 (1989) can be employed to introduce and select for the presence of inactivated genes in other eukaryotes, including plant and mammalian species. Cells or derived organisms (Cappechi, supra) that contain only inactivated copies of the squalene synthetase coding region may be advantageous in over-production of numerous mevalonate-derived non-sterol isoprene compounds that are produced at only moderate levels in wild-type cells. For example, insect cells so modified may produce higher levels of juvenile hormone, plant cells such as tobacco may produce more phytoalexins and *Hevea brasilensis* cells may produce more rubber. All these effects would be secondary to the inactivation of squalene synthetase activity and consequent diversion of cellular FPP pools away from sterol synthesis. Cells or organisms produced as above may also prove useful in screens to identify inhibitors of squalene synthetase, or of other enzymes that use FPP as a substrate.

The present invention further concerns expression vectors comprising a DNA sequence coding for all or part of squalene synthetase. The expression vectors preferably contain all or part of one of the DNA sequences having the nucleotide sequences substantially as shown in FIGS. 2, 8 or 9. Further preferred are expression vectors comprising one or more regulatory DNA sequences operatively linked to the DNA sequence coding for all or part of squalene synthetase. As used in this context, the term "operatively linked" means that the regulatory DNA sequences are capable of directing the replication and/or the expression of the DNA sequence coding for all or part of squalene synthetase. Also preferred are expression vectors comprising a DNA sequence coding for a modified squalene synthetase in which the carboxy terminal transmembrane sequence has been removed. Additionally preferred are expression vectors comprising a DNA sequence which has been modified (e.g., disrupted, deleted or truncated) so as to code for a squalene synthetase molecule which is not catalytically active.

Expression vectors of utility in the present invention are often in the form of "plasmids", which refer to circular double stranded DNA loops which, in their vector form, are not bound to the chromosome. However, the invention is intended to include such other forms of expression vectors which serve equivalent functions and which become known in the art subsequently hereto.

Expression vectors useful in the present invention typically contain an origin of replication, a promoter located in front of (i.e., upstream of) the DNA sequence and followed by the DNA sequence coding for all or part of squalene synthetase, transcription termination sequences and the remaining vector. The expression vectors may also include other DNA sequences known in the art, for example, stability leader sequences which provide for stability of the expression product, secretory leader sequences which provide for secretion of the expression product, sequences which allow expression of the structural gene to be modulated (e.g., by the presence or absence of nutrients or other inducers in the growth medium), marking sequences which are capable of providing phenotypic selection in transformed host cells, stability elements such as centromeres which provide mitotic stability to the plasmid, and sequences which provide sites for cleavage by restriction endonucleases. The characteristics of the actual expression vector used must be compatible with the host cell which is to be employed. For example, when cloning in a mammalian cell system, the expression vector should contain promoters isolated from the genome of mammalian cells, (e.g., mouse metallothionien promoter), or from viruses that grow in these cells (e.g., vaccinia virus 7.5K promoter). An expression vector as contemplated by the present invention is at least capable of directing the replication, and preferably the expression, of the DNA sequences of the present invention. Suitable origins of replication include, for example, a yeast ARS element, a COLEI ori element, and an SV40 ori element. Suitable promoters include, for example, the yeast GAL1 promoter, the synthetic bacterial Tac promoter, the SV40 early promoter and the baculovirus AcNPV polyhedrin promoter. Suitable termination sequences include, for example, the yeast cycl terminator, the bacterial rrnB terminator, and the SV40 3' polyA' signal segment. As selectable markers, kanamycin resistance, uracil (URA3) marker and neomycin resistance can be employed. All of these materials are known in the art and are commercially available.

Particularly preferred is the expression vector designated pSM60, described herein below, which contains the DNA sequence coding for yeast squalene synthetase, or expression vectors with the identifying characteristics of pSM60.

A host cell (*Saccharomyces cerevisiae* strain SGY 1204) containing pSM60 was deposited with the American Type Culture Collection, Rockville, Md. on Sep. 21, 1990 under the Budapest Treaty and assigned ATCC accession no. 74019.

Suitable expression vectors containing the desired coding and control sequences may be constructed using standard recombinant DNA techniques known in the art, many of which are described in Maniatis, T. et al., *Molecular Cloning: A Laboratory Manual,* Cold Spring Harbor Laboratory, Cold Spring Harbor, N.Y. (1982).

The present invention additionally concerns host cells containing an expression vector which comprises a DNA sequence coding for all or part of squalene synthetase. The host cells preferably contain an expression vector which comprises all or part of one of the DNA sequence having the nucleotide sequences substantially as shown in FIGS. 2, 8 or 9. Further preferred are host cells containing an expression vector comprising one or more regulatory DNA sequences capable of directing the replication and/or the expression of and operatively linked to a DNA sequence coding for all or part of squalene synthetase. Also preferred are host cells containing an expression vector which comprises a DNA sequence coding for a modified squalene synthetase in which the carboxy terminal transmembrane sequence has been removed. Additionally preferred are host cells containing an expression vector which comprises a DNA sequence which has been modified (e.g., disrupted, deleted or truncated) so as to code for a squalene synthetase molecule which is not catalytically active. Suitable host cells include both prokaryotic and eukaryotic cells. Suitable prokaryotic host cells include, for example, *Escherichia coli, Bacillus subtilus* and *Streptomyces coelicolor* cells. Suitable eukaryotic host cells include, for example, *Saccharomyces cerevisiae*, COS monkey cells, *S. pombe, S. frugiperda* insect cells, CHO hamster cells and mouse pluripotent stem cells.

Particularly preferred as host cells are *Saccharomyces cerevisiae* GAL+ strains.

Expression vectors may be introduced into host cells by various methods known in the art. For example, transfection of host cells with expression vectors can be carried out by the calcium phosphate precipitation method. However, other methods for introducing expression vectors into host cells, for example, electroporation, biolistic fusion, liposomal fusion, nuclear injection, viral or phage infection or protoplast fusion, can also be employed.

Once an expression vector has been introduced into an appropriate host cell, the host cell may be cultured under conditions permitting expression of large amounts of the desired polypeptide, in this case a polypeptide molecule comprising all or part of squalene synthetase. Such polypeptides are useful in the study of the characteristics of squalene synthetase, for example, its role in cholesterol biosynthesis.

Host cells containing an expression vector which contains a DNA sequence coding for all or part of squalene synthetase may be identified by one or more of the following six general approaches: (a) DNA-DNA hybridization; (b) the presence or absence of marker gene functions; (c) assessing the level of transcription as measured by the production of squalene synthetase mRNA transcripts in the host cell; (d) detection of the gene product immunologically; (e) complementation analysis; and (f) enzyme assay, enzyme assay being the preferred method of identification.

In the first approach, the presence of a DNA sequence coding for all or part of squalene synthetase can be detected by DNA-DNA or RNA-DNA hybridization using probes complementary to the DNA sequence.

In the second approach, the recombinant expression vector host system can be identified and selected based upon the presence or absence of certain marker gene functions (e.g., thymidine kinase activity, resistance to antibiotics, uracil prototrophy, etc.). A marker gene can be placed in the same plasmid as the DNA sequence coding for all or part of squalene synthetase under the regulation of the same or a different promoter used to regulate the squalene synthetase coding sequence. Expression of the marker gene in response to induction or selection indicates expression of the DNA sequence coding for all or part of squalene synthetase.

In the third approach, the production of squalene synthetase mRNA transcripts can be assessed by hybridization assays. For example, polyadenylated RNA can be isolated and analyzed by Northern blotting or nuclease protection assay using a probe complementary to the RNA sequence. Alternatively, the total nucleic acids of the host cell may be extracted and assayed for hybridization to such probes.

In the fourth approach, the expression of all or part of squalene synthetase can be assessed immunologically, for example, by Western blotting.

In the fifth approach, the expression of squalene synthetase protein can be assessed by complementation analysis. For example, in cells known to be deficient in this enzyme, expression of squalene synthetase activity can be inferred by improved growth of cells under growth-limiting conditions, such as sterol deprivation.

In the sixth approach, expression of squalene synthetase can be measured by assaying for squalene synthetase enzyme activity using known methods. For example, the assay described in Biller, S. A. et al., J. Med. Chem. 31, 1869 (1988) may be employed.

The DNA sequences of expression vectors, plasmids or DNA molecules of the present invention may be determined by various methods known in the art. For example, the dideoxy chain termination method as described in Sanger et al., Proc. Natl. Acad. Sci. USA 74, 5463–5467 (1977), or the Maxam-Gilbert method as described in Proc. Natl. Acad. Sci. USA 74, 560–564 (1977) may be employed.

It should, of course, be understood that not all expression vectors and DNA regulatory sequences will function equally well to express the DNA sequences of the present invention. Neither will all host cells function equally well with the same expression system. However, one of ordinary skill in the art may make a selection among expression vectors, DNA regulatory sequences, and host cells using the guidance provided herein without undue experimentation and without departing from the scope of the present invention.

The present invention further concerns a method for detecting a nucleic acid sequence coding for all or part of squalene synthetase or a related nucleic acid sequence comprising contacting the nucleic acid sequence with a detectable marker which binds specifically to at least a portion of the nucleic acid sequence, and detecting the marker so bound. The presence of bound marker indicates the presence of the nucleic acid sequence. Preferably, the nucleic acid sequence is a DNA sequence having all or part of one of the nucleotide sequences substantially as shown in FIGS. 2, 8 or 9. Also preferred is a method in which the DNA sequence is a genomic DNA sequence. A DNA sample containing the DNA sequence may be isolated using various methods for DNA isolation which are well-known to those of ordinary skill in the art. For example, a genomic DNA sample may be isolated from tissue by rapidly freezing the tissue from which the DNA is to be isolated, crushing the tissue to produce readily digestible pieces, placing the crushed tissue in a solution of proteinase K and sodium dodecyl sulfate, and incubating the resulting solution until most of the cellular protein is degraded. The digest is then deprotenized by successive phenol/chloroform/isoamyl alcohol extractions, recovered by ethanol precipitation, and dried and resuspended in buffer.

Also preferred is the method in which the nucleic acid sequence is an RNA sequence. Preferably, the RNA sequence is an mRNA sequence. Additionally preferred is the method in which the RNA sequence is located in the cells of a tissue sample. An RNA sample containing the RNA sequence may be isolated using various methods for RNA isolation which are well-known to those of ordinary skill in the art. For example, an RNA sample may be isolated from cultured cells by washing the cells free of media and then lysing the cells by placing them in a 4M guanidinium solution. The viscosity of the resulting solution is reduced by drawing the lysate through a 20 gauge needle. The RNA is then pelleted through a $CsCl_2$ step gradient, and the supernatant fluid from the gradient carefully removed to allow complete separation of the RNA, found in the pellet, from contaminating DNA and protein.

The detectable marker useful for detecting a nucleic acid sequence coding for all or part of squalene synthetase or a related nucleic acid sequence, may be a labeled DNA sequence, including a labeled cDNA sequence, having a nucleotide sequence complementary to at least a portion of the DNA sequence coding for all or part of squalene synthetase.

The detectable marker may also be a labeled sense or antisense RNA sequence having a nucleotide sequence complementary to at least a portion of the DNA sequence coding for all or part of squalene synthetase.

The detectable markers of the present invention may be labeled with commonly employed radioactive labels, such as $^{32}P$ and $^{35}S$, although other labels such as biotin or mercury may be employed. Various methods well-known to those of ordinary skill in the art may be used to label the detectable markers. For example, DNA sequences and RNA sequences may be labeled with $^{32}P$ or $^{35}S$ using the random primer method.

Once a suitable detectable marker has been obtained, various methods well-known to those of ordinary skill in the art may be employed for contacting the detectable marker with the sample of interest. For example, DNA-DNA, RNA-RNA and DNA-RNA hybridizations may be performed using standard procedures known in the art. In a typical DNA-DNA hybridization procedure for detecting DNA sequences coding for all or part of squalene synthetase in genomic DNA, the genomic DNA is first isolated using known methods, and then digested with one or more restriction enzymes. The resulting DNA fragments are separated on agarose gels and denatured in situ. After prehybridization to reduce nonspecific hybridization, a radiolabeled nucleic acid probe is hybridized to the immobilized DNA fragments. The filter is then washed to remove unbound or weakly bound probe, and is then autoradiographed to identify the DNA fragments that have hybridized with the probe.

The presence of bound detectable marker may be detected using various methods well-known to those of ordinary skill in the art. For example, if the detectable marker is radioactively labeled, autoradiography may be employed. Depending on the label employed, other detection methods such as spectrophotometry may also be used.

It should be understood that nucleic acid sequences related to nucleic acid sequences coding for all or part of squalene synthetase can also be detected using the methods described herein. For example, a DNA probe based on conserved regions of yeast squalene synthetase (e.g., the catalytic site) can be used to detect and isolate related DNA sequences (e.g., a DNA sequence coding for human squalene synthetase). All such methods are included within the scope of the present invention.

As used in the present application and in this context, the term "related" means a nucleic acid sequence which is able to hybridize to an oligonucleotide probe based on the nucleotide sequence of squalene synthetase.

The present invention further concerns methods for detecting substrates or inhibitors of squalene synthetase. In particular, the present invention concerns a method for detecting a substrate or inhibitor of squalene synthetase comprising:

(a) culturing separately a host cell deficient in squalene synthetase containing an expression vector coding for squalene synthetase and a host cell deficient in squalene synthetase containing an expression vector coding for a partially defective squalene synthetase;

(b) contacting and incubating the host cells with a sample thought to contain a substrate or inhibitor of squalene synthetase; and (c) determining the effect of the sample thought to contain a substrate or inhibitor of squalene synthetase on the host cells.

In this case, if a sample contains an inhibitor of squalene synthetase, growth of the host cell containing an expression vector coding for squalene synthetase will not be as greatly inhibited as growth of the host cell containing an expression vector coding for a partially defective squalene synthetase.

It is preferred that the host cells used in this method be a strain of *Saccharomyces cerevisiae*.

Substrates or inhibitors of squalene synthetase identified by this methodology may be potential cholesterol lowering drugs. See for example U.S. Pat. No. 4,871,721 which issued on Oct. 3, 1989, which describes squalene synthetase inhibitors.

The present invention further concerns polypeptide molecules comprising all or part of squalene synthetase, said polypeptide molecules preferably having all or part of one of the amino acid sequences substantially as shown in FIGS. 2, 8 or 9. Also preferred are modified squalene synthetase molecules in which the carboxy terminal transmembrane sequence has been removed. In the case of polypeptide molecules comprising part of squalene synthetase, it is preferred that polypeptide molecules be at least about 8 amino acids in length.

All amino acid residues identified herein are in the natural L-configuration. In keeping with standard polypeptide nomenclature, J. Biol. Chem. 243, 3557–3559 (1969), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | T-asparagine |
| C | Cys | L-cysteine |

All amino acid sequences are represented herein by formulas whose left to right orientation is in the conventional direction of amino-terminus to carboxy-terminus.

The polypeptides of the present invention may be obtained by synthetic means, i.e., chemical synthesis of the polypeptide from its component amino acids, by methods known to those of ordinary skill in the art. For example, the solid phase procedure described by Houghton et al., Proc. Natl. Acad. Sci. 82, 5135 (1985) may be employed. It is preferred that the polypeptides be obtained by production in prokaryotic or eukaryotic host cells expressing a DNA sequence coding for all or part of squalene synthetase, or by in vitro translation of the mRNA encoded by a DNA sequence coding for all or part of squalene synthetase. For example, the DNA sequence of FIG. 2 may be synthesized using PCR as described above and inserted into a suitable expression vector, which in turn may be used to transform a suitable host cell. The recombinant host cell may then be cultured to produce squalene synthetase. Techniques for the production of polypeptides by these means are known in the art, and are described herein.

The polypeptides produced in this manner may then be isolated and purified to some degree using various protein purification techniques. For example, chromatographic procedures such as ion exchange chromatography, gel filtration chromatography and immunoaffinity chromatography may be employed.

The polypeptides of the present invention may be used in a wide variety of ways. For example, the polypeptides may be used to prepare in a known manner polyclonal or monoclonal antibodies capable of binding the polypeptides. These antibodies may in turn be used for the detection of the polypeptides of the present invention in a sample, for example, a cell sample, using immunoassay techniques, for example, radioimmunoassay or enzyme immunoassay. The antibodies may also be used in affinity chromatography for purifying the polypeptides of the present invention and isolating them from various sources.

The polypeptides of the present invention have been defined by means of determined DNA and deduced amino acid sequencing. Due to the degeneracy of the genetic code, other DNA sequences which encode the same amino acid sequence as depicted in FIG. 2 may be used for the production of the polypeptides of the present invention. In addition, it will be understood that allelic variations of these DNA and amino acid sequences naturally exist, or may be intentionally introduced using methods known in the art. These variations may be demonstrated by one or more amino acid differences in the overall sequence, or by deletions, substitutions, insertions, inversions or additions of one or more amino acids in said sequence. Such amino acid substitutions may be made, for example, on the basis of similarity in polarity, charge, solubility, hydrophobicity, hydrophilicity and/or the amphiphathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Other contemplated variations include salts and esters of the aforementioned polypeptides, as well as precursors of the aforementioned polypeptides, for example, precursors having N-terminal substituents such as methionine, N-formylmethionine and leader sequences. All such variations are included within the scope of the present invention.

The following examples are further illustrative of the present invention. These examples are not intended to limit the scope of the present invention, and provide further understanding of the invention.

EXAMPLE 1

Cloning and Characterization of Yeast Squalene Synthetase Gene

A yeast genomic library was constructed using plasmid YEp351 (5.6 kb) obtained from Dr. A. Tzagoloff (Columbia University, New York, N.Y.) as the vector. This vector is described in Yeast 2, 163–167 (1986). This library was made by insertion of approximately 4.5 kb-sized Sau3A partial fragments of chromosomal DNA from the yeast strain SGY58 (MATaleu2-4lys2 cir°; Squibb Genetic Yeast Collection, Princeton, N.J.) into the Bam HI site of the phosphatased YEp351 vector. A pool of about 14,000 E. coli Amp$^R$ transformants were amplified to obtain library DNA for yeast transformation by replating on ampicillin plates to prevent selective loss of clones. Analysis of the library by restriction enzyme mapping of 20 independent clones showed that it contained 90% recombinant plasmids and possessed a high degree of clone heterogeneity. Based on a 15 Megabase estimate for the size of the yeast genome, this library (henceforth the SCB-library) overrepresented the yeast genome by a factor of 3.5.

Large scale (200 plate/experiment) transformations of the erg9 strain SGY1011 (Squibb Genetic Yeast Collection) were done using SCB-library DNA and yielded a total of over 200,000 LEU$^+$ transformants. Transformations were performed by electroporation using a Gene Pulser (Bio-Rad Laboratories, Richmond, Calif.). Three sequential pulses of field strength 1.0 kV/cm were delivered to $10^9$ yeast cells in the presence of 30 µg of library DNA in 0.5 ml of 35% polyethylene glycol (PEG). LEU+ transformants were selected by embedding electroporated cells in regeneration agar containing 20 µg/ml ergosterol and incubating anaerobically at 28° C. for 5 days. Since there were only 14,000 clones in the original SCB-library pool, each clone was represented 15 times in the LEU$^+$ transformant pool. To select for erg9 cells that were functionally complemented for their squalene synthetase defect, the erg9 transformant pool was plated onto selective agar lacking ergosterol. Following aerobic growth at 30° C. for three days most of the cells formed micro-colonies that contained senescent yeast. However, approximately two out of every $10^4$ cells plated formed large continuously growing colonies. To verify that they were not simply wild-type contaminant yeast, 100 of the large colonies were streaked onto minimal agar without nutritional supplements. As expected for bona fide erg9 strain transformants, the cells failed to grow on this agar. To verify that the large colonies did not represent mutational revertants (erg9→ERG9) of the original erg9 strain, plasmid curing experiments were carried out. Twenty large LEU$^+$ colonies were cured of their plasmids by growth for several generations on rich medium containing ergosterol. Cured (leu$^-$) cells were then streaked onto selective agar without ergosterol and grown aerobically; in all cases they failed to form colonies. Thus, concomitant with the loss of LEU$^+$ plasmids, the cells displayed the ergosterol-auxotrophy characteristic of the erg9 mutant strain, indicating that the erg9 mutation had not reverted in these cells.

To reduce the number of candidate ERG9 clones, LEU$^+$ plasmids from twelve large colonies were characterized by restriction enzyme digestion. This analysis showed that eleven of the plasmids contained three different yeast DNA inserts of 4.5 kb, 5.6 kb and 2.4 kb and these plasmids were designated pSM51, pSM52 and pSM53, respectively. As indicated in FIG. 1, these plasmids shared a 2.0 kb region.

When yeast genes are cloned by functional complementation of mutant cells (as above), plasmids are sometimes isolated that contain "suppressor elements" which partially ameliorate the underlying genetic defect. Usually, such translational suppression is inefficient (resulting in 1–10% of wild-type enzyme levels) and is seen only with multicopy yeast plasmids. To check whether the putative ERG9 plasmids isolated above contained suppressor elements, several complementated erg9 cells were examined biochemically. Cell-free enzyme extracts were prepared from a wild-type strain (ERG9), from an untransformed erg9 strain and from the erg9 mutant strain bearing the putative ERG9 plasmids by disruption of yeast with glass beads (0.45 micron). Briefly, cells were harvested, washed once with distilled water and disrupted by vortexing vigorously in the presence of 4° C. breakage buffer (0.1M Tris-HCl, pH 7.5/10 mM 2-mercaptoethanol). Cell debris was removed by 10 min centrifugation at 4000 rpm and the 4000× g supernatant fractions (S4k) were then used for in vitro $^{14}$C-IPP (isopentenyl pyrophosphate) conversion reactions to measure incorporation into sterol precursors, predominantly squalene. Reaction mixtures contained, in a total volume of 0.2 ml, 5 mM $MgCl_2$, 4 mM ATP, 1 mM NADPH, 10 mM KF, 100 mM Tris-hydrochloride, pH 7.5, 0.1 µCi of [1-$^{14}$C]-isopentenyl pyrophosphate (56 mCi/mmole) and 0.15 ml of the S4k fraction. Reactions were incubated at 37° C. for 20 minutes and terminated by the addition of 0.8 ml $CHCl_3$: methanol (2:1 vol/vol). The phases were vortexed briefly and separated by low speed centrifugation. The organic phase was removed, washed twice with methanol, and the organic-extractable products were analyzed by thin layer chromatography (TLC) using Merck LK6D plates developed with dichloromethane. This experiment showed that the wild-type strain and two of the complemented strains made large amounts of squalene. By contrast, the erg9 strain made none and produced mostly farnesol, a breakdown product of FPP. The third complemented strain, that contained pSM53, made small amounts of squalene but also some farnesol, suggestive of partial complementation. These findings were verified in studies where microsomal membranes prepared from each of the strains above were assayed for squalene synthetase activity using a gas chromatographic (GC) method of squalene quantitation. Briefly, squalene synthetase activity in microsomal membranes prepared from yeast was assayed at 30° C. under $N_2$ in 2.0 ml of buffer containing 50 mM $KPO_4$, 5 mM $MgCl_2$, 0.9 mM NADPH, 22 µM FPP, 10 mM KF, 0.1 mM EDTA and 0.8 mM 2-mercaptoethanol. Reaction products were saponified, hexane-extracted and analyzed for squalene levels using a gas chromatographic assay as described in Biller, S. A. et al., supra. These studies showed that erg9 cells bearing plasmids pSM51 and pSM52 possessed at least wild-type levels of enzyme, whereas those bearing pSM53 had only 5% of wild-type levels. Untransformed erg9 mutant cells had no detectable enzyme activity.

To further localize the ERG9 gene on plasmid pSM51, two subclones were created using standard recombinant DNA techniques. Plasmids pSM54 and pSM55 contained a 2.4 kb XbaI fragment of pSM51 cloned in opposite orientations in the low copy-number vector YCp50LEU (Squibb Genetic Bacteria Collection, Princeton, N.J.). The yeast inserts on these plasmids contained 400 bp of DNA not present on pSM53. Biochemical analysis of cell-free extracts from pSM54 and pSM55-transformed erg9 cells by the $^{14}$C-IPP conversion assay described above showed that both plasmids completely complemented the squalene synthetase defect of the strain, demonstrating that a single copy of the gene could correct the erg9 defect.

The nucleotide sequences of both the coding and noncoding strands were determined by the dideoxy chain termination method as described in Sanger, et al., supra using modified T7 DNA polymerase (U.S. Biochemical Corp., Cleveland, Ohio). Subclones of a 2.4 kb XbaI-BamHI fragment from pSM54 generated in M13mp18 and mp19 using various restriction fragments were used for these reactions. The sequence was confirmed in reactions using 34 base oligonucleotides that hybridized to the ERG9 gene at 250 base intervals as primers. A single open reading frame (ORF) of 1065 bp was present on the insert from pSM53; however, sequencing of 5'-contiguous DNA from pSM51 extended the pSM53 ORF to 1332 bp. This larger ORF predicted a protein of 444 amino acids with a $M_r$ of 51,753 (FIG. 2), in good agreement with recent size estimates for squalene synthetase in yeast. The amino-terminus of the ERG9 protein remains provisional, since there are two in-frame methionine codons at positions 1 and 13 of the amino acid sequence. As described above, pSM51 and pSM52-transformed erg9 cells possessed wild-type levels of enzyme, whereas cells bearing pSM53 contained at most, 5% of those levels. The smaller ORF on the pSM53 clone probably represents an aberrant ERG9 gene whose 5'-upstream and 5'-translated sequences were truncated during construction of the genomic library.

Examination of the sequences immediately adjacent to the putative ERG9 translational start codon revealed a series of alternating purines and pyrimidines extending for twelve nucleotides. Similar sequences have been reported upstream of numerous other yeast start codons, suggesting that the ERG9 ATG assignment may be the correct one. A consensus TATA transcriptional regulatory element was located 100 nucleotides upstream of the ERG9 ATG but no direct or inverted repeats, often associated with upstream activator sequence (UAS) elements, were found.

EXAMPLE 2

Northern Blot Analysis

To confirm the direction of transcription and determine the size of the ERG9 transcript, a Northern blot analysis of total mRNA from a wild-type (ERG9) and an ERG9::HIS3 deletion yeast strain was performed. Yeast cells grown anaerobically in YEPD medium containing 20 µg/ml ergosterol were lysed by vortexing with glass beads in the presence of phenol/chloroform. Total RNA was purified by repeated extraction with phenol/chloroform, ethanol precipitated, and separated on a 0.9% agarose gel containing 50% formaldehyde. The gel was blotted onto a nitrocellulose membrane by the method of Southern, E. M., J. Mol. Biol. 98, 503–517 (1975) and hybridized with a $^{32}$P-labeled, single stranded probe that was prepared by nick-translation of a 1.0 kb EcoR1-ScaI fragment from pSM53. The membrane was hybridized with the probe at 42° C. in 50% formamide, 0.25M $NaH_2PO_4$, pH 7.2, 0.25M NaCl, 1 mM EDTA, 7% SDS and 100 ng/ml calf thymus DNA for 16 hours, washed at 62° C. in SSPE (0.15M NaCl, 10 mM $NaH_2PO_4$, pH 7.4 and 1 mM EDTA) for 30 minutes, and auto-radiographed with X-ray film at −70° C. for 18 hours.

A single transcript of approximately 1.8 kb was detected (FIG. 3) using the ERG9-specific single stranded probe.

EXAMPLE 3

Hydrophobicity Analysis

Figure 4:
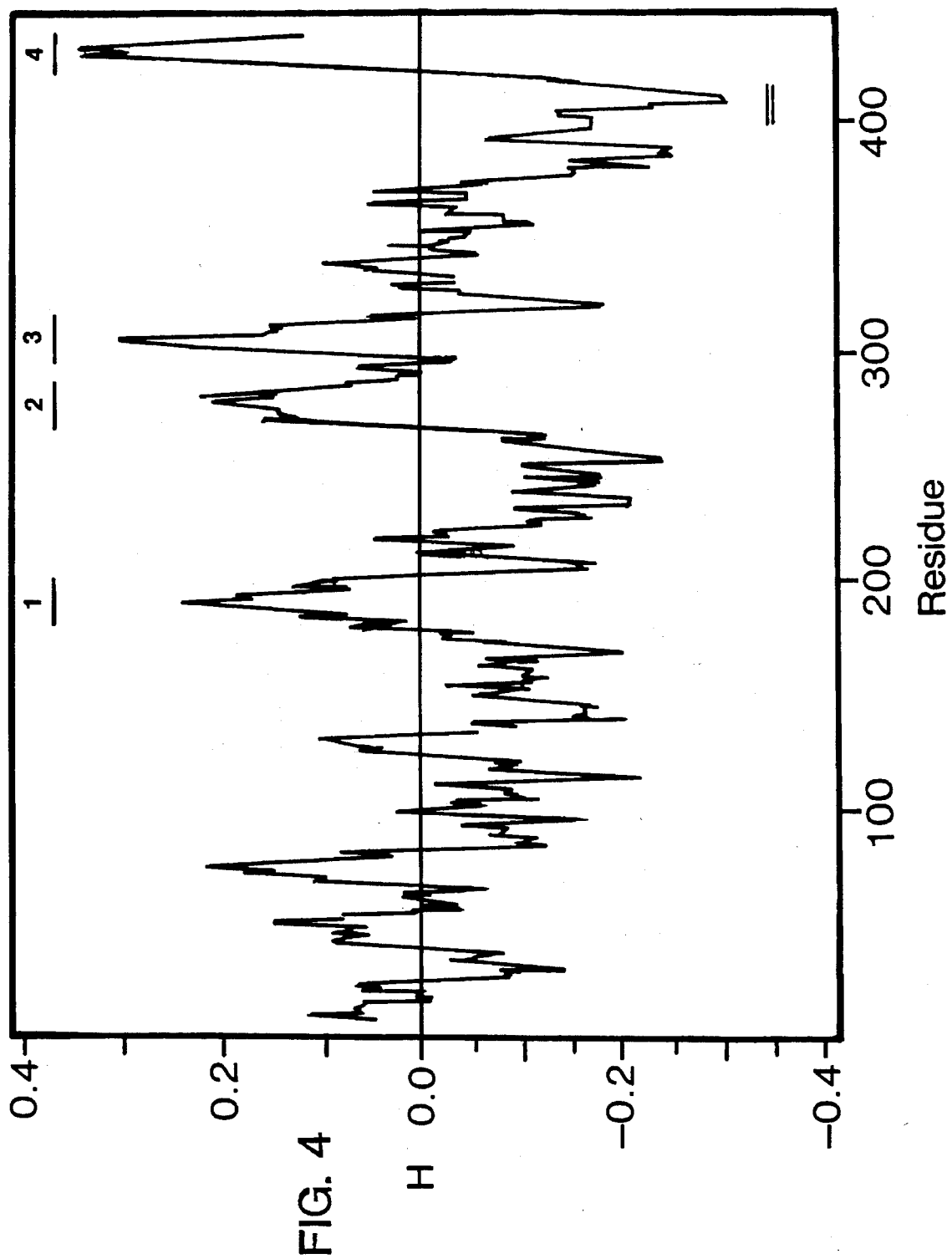
FIG. 4 shows a hydrophobicity plot of the amino acid sequence of yeast squalene synthetase. The hydrophobicity of each residue is plotted as a function of residue number. Hydrophobic regions that are predicted to be membrane-associated according to the criteria of Eisenberg, D. et al., J. Mol. Biol. 178, 125 (1984) are labeled 1 through 4 and contain the underlined sequences in FIG. 2. A hydrophilic region that contains a "PEST" sequence is double-underlined.

Because squalene synthetase is a membrane-bound enzyme, its primary structure was examined for hydrophobic domains that could serve as membrane transit peptides or transmembrane segments. The hydrophobicity of each residue was calculated using the "SOAP" program of Kyte and Doolittle [Kyte, J. et al., J. Mol. Biol. 157, 105 (1982)] with a window size of 15 amino acids. A hydrophobicity plot (FIG. 4) revealed several very hydrophobic regions in the protein, four of which met the criteria of Eisenberg et al., supra for the prediction of membrane-associated helices. They are centered at amino acids 187, 275, 301, and 431. Although all of these domains are of sufficient length (21 residues) to form a 30 A° ∝-helix, a hydrophobic moment plot classified only the third domain as a transmembrane sequence and the others as membrane-proximal sequences. The algorithm of Rao and Argos [Rao, J. K. M., et al., Biochem. Biophys. Acta 869, 197 (1986)] was also applied to the prediction of membrane-spanning helices and identified both the third and fourth domains as transmembrane sequences. Interestingly, the fourth (COOH-terminal) domain of squalene synthetase is the most hydrophobic one and resembles a "simple" eukaryotic transmembrane domain found in proteins containing only a single membrane-spanning sequence. Such sequences are usually located within 40 residues of the carboxy-terminus, lack Asn, Gln, His, Trp, Pro and all charged amino acids, and are immediately followed by multiple positively charged residues. In the absence of experimental evidence supporting one secondary structure over another, a simple model is favored in which only the fourth domain is used as a transmembrane tether. In this model, almost the entire squalene synthetase protein could project from the cytoplasmic surface of the endoplasmic reticulum membrane, where the enzyme is known to function. The three other domains could conceivably serve as hydrophobic pockets in the protein and be used for binding the isoprene moieties of two FFP molecules during catalysis.

Although little is known about the in vivo regulation of squalene synthetase in yeast, a potential regulatory site was identified from the primary sequence. The amino acid sequence, YDDELVPTQQEEEY (FIG. 2, 402–415), located just proximal to the fourth hydrophobic domain, is a strong candidate for a "PEST" site. PEST sequences are regions at least ten amino acids long that are highly enriched in proline, glutamic acid, aspartic acid, serine and threonine residues, whose presence in many proteins has been associated with rapid intracellular turnover. A PEST sequence often contains potential sites for phosphorylation by casein kinase II and adenosine 3', 5'-monophosphate (cAMP)-dependent protein kinase, which may be used by the cell to regulate protein-specific degradation by proteases such as calpains. HMG CoA reductase (HMGR) from many species, including yeast, contains very strong PEST sequences in the "linker region" between its multiple membrane-spanning domains and its catalytic domain. HMGR is also rapidly degraded in mammalian cells when they become satiated with cholesterol and the HMGR PEST sequences are very close to a major protease cleavage site. If the proposed, single membrane-spanning model for squalene synthetase is correct, the ERG9 PEST sequence would likely be located within a comparable linker region, suggesting the possibility of parallel architecture and turnover of this enzyme and HMGR. Consistent with this hypothesis, two sites for casein kinase II phosphorylation are located close to the PEST sequence (Ser$^{400}$ and Thr$^{409}$), as well as at other positions within the protein. A potential site for tyrosine kinase phosphorylation (Tyr$^{402}$) is also present within this region.

EXAMPLE 4

Disruption of ERG9 Gene

Figure 5:
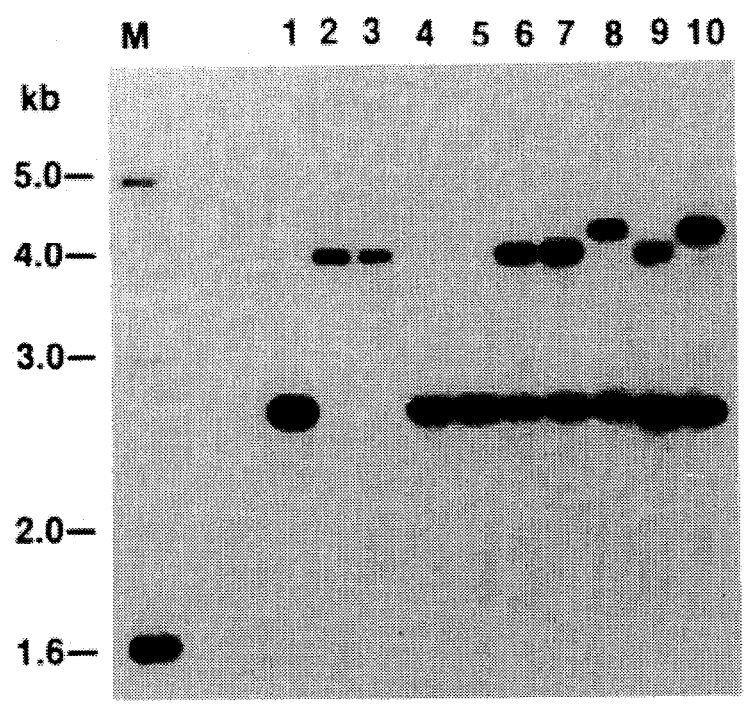
FIG. 5 shows the disruption of the ERG9 gene in a diploid yields haploids that are strict ergosterol auxotrophs. M, markers; DNA from undisrupted SGY1161 (lane 1) or HIS3-disrupted SGY1161 (lane 6) and DNA from four haploids (lanes 2–5) derived from HIS3-disrupted SGY1161; DNA from SGY969 that was HIS3-disrupted (lanes 7 and 9) or LEU2-disrupted (lanes 8 and 10).

The ability to engineer chromosomal disruptions of cloned genes in yeast permitted an investigation of the role of squalene synthetase in sterol metabolism and cell growth. Southern hybridization experiments performed with chromosomal DNA from a diploid strain indicated that the ERG9 gene is present at just a single locus in S. cerevisiae (FIG. 5). To produce gene disruptions, plasmids pET105 and pET106 were created from pSM52 (FIG. 1) by replacement of a 1.0 kb EcoR1-Sca1 fragment of the ERG9 coding region with either a 1.5 kb EcoR1-EcoR5 HIS3 (encoding imidazoleglycerol-phosphate dehydratase) fragment from YEp6 (Squibb Genetic Bacteria Collection, Princeton, N.J.) or a 1.7 kb EcoR1-Sca1 LEU2 (encoding β-isopropylmalate dehydrogenase) fragment from YEp13 (Squibb Genetic Bacteria Collection, Princeton, N.J.) using standard recombinant DNA techniques. The insertionally-inactivated ERG9 genes of pET105 and pET106 were then used to replace chromosomal alleles in yeast by the one-step gene disruption method of Rothstein, R. J., Meth. Enzymol. 101, 202 (1983). Linear fragments suitable for homologous recombination at the ERG9 locus were generated by restriction digestion (described below) and used to transform spheroplasted diploid strains by electroporation as described above to either histidine or leucine prototrophy. Transformants were screened to identify those bearing the ERG9 disruption by probing chromosomal DNA with a 1.1 kb Sca1-Xba1 restriction fragment that spans the 3'-end of the ERG9 gene. Briefly, chromosomal DNA prepared as described in Maniatis, et. al. supra, from diploid disruption strain was digested with XbaI, electrophoresed on a 0.8% agarose gel, blotted to Bio-Trans membrane (ICN Biomedicals, Inc., Irvine, Calif.) and probed with an ERG9 probe as described in Maniatis, et al. supra. From among the transformants, five were picked for further study because they yielded the pattern of Xba1 restriction fragments expected to arise from single copy integrations of either the HIS3 or LEU2 gene into an ERG9 allele of a diploid (FIG. 5). Xba1 fails to cut within the ERG9 coding region or within the HIS3 or LEU2 marker fragments used to disrupt the ERG9 gene. Thus in ERG9::HIS3 disruption strains, a wild-type ERG9 allele with a reactive band of 2.7 kb is replaced with a band of 4.2 kb. Similarly, in ERG9::LEU2 disruption strains, the 2.7 kb band is replaced with a reactive band of 4.4 kb.

The ERG9 gene disruptions were constructed as described above in two diploid strains; the homozygous strain SGY1161 (Squibb Genetic Yeast Collection; genotype: ERG9/ERG9) and the heterozygous strain SGY969 (Squibb Genetic Yeast Collection; genotype: ERG9/erg9). These strains were transformed by electroporation as described above using an Sst1-Sph1 restriction digestion fragment of pET105 (SGY1161) or pET106 (SGY969) DNA. All of the His+ or Leu+ prototrophs recovered from transformation of strain SGY1161 were ergosterol prototrophs, indicating that a disrupted ERG9 allele is recessive to an undisrupted one. In contrast, approximately half of the transformants obtained with strain SGY969 were found to be auxotrophic for ergosterol. This was the expected result if half of the integration events caused a disruption of the ERG9 and half a disruption of the erg9 allele in this diploid.

Figure 3:
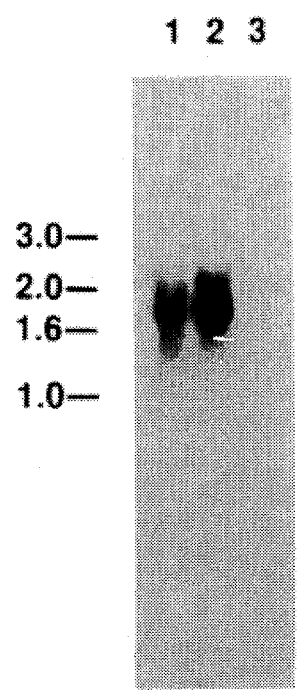
FIG. 3 shows a Northern blot analysis of ribonucleic acid (RNA) from wild-type and mutant yeast strains.

To further examine the cellular consequences of ERG9 gene disruption, His+ and Leu+ transformants of diploid strain SGY1161 were sporulated on nitrogen-starvation agar using standard methods. Using a microscope and a fine glass needle attached to a micromanipulator, four-spored tetrads were dissected so as to isolate the individual spores for growth on YEPD plates. After 6 days of growth at 30° C., no more than two spores from each tetrad were viable. To recover the presumed ERG9-disruption spores, tetrad dissection was repeated using YEPD medium supplemented with ergosterol, and plates were incubated anaerobically to promote sterol uptake. Under these conditions, SGY1161 and the disrupted diploids yielded predominantly tetrads with four viable spores; spores that failed to germinate were comparable among tetrads from disrupted and undisrupted diploids. In tetrads dissected from undisrupted SGY1161, all four spores were prototrophic for ergosterol and auxotrophic for both leucine and histidine (Table 1). Tetrads from a HIS disruption of SGY1161 displayed the 2 His+:2 His– pattern expected for segregation of a heterozygous marker. Significantly, ergosterol auxotrophy segregated 2 Erg+:2 Erg– and all the Erg– spores were also His+, demonstrating that the Erg– phenotype was tightly linked to the ERG9::HIS3 disruption. Identical results were obtained from a genetic analysis of the LEU2 disruption diploid (Table 1). Southern blot analysis conducted as described above on chromosomal DNA from four spores from a HIS3 disruption tetrad confirmed that disrupted and wild-type ERG9 alleles segregated 2:2 (FIG. 5). Biochemical assays of cell-free extracts prepared from two complete set of tetrads also showed that all His+ spores completely lacked squalene synthetase activity. Finally, Northern analysis of mRNA from a His+ haploid showed that a normal ERG9 transcript was missing in these cells (FIG. 3).

These experiments demonstrate that squalene synthetase activity is necessary for vegetative growth of haploid yeast cells, but that the requirement for this enzyme can be bypassed when exogenous ergosterol is provided. Deletion of either of the structural genes for two enzymes that follow squalene synthetase in the sterol pathway, squalene epoxidase (ERG1) or lanosterol demethylase (ERG16), also leads to ergosterol auxotrophy in yeast. However, ERG9 null mutants may be especially useful for exploring the regulation of isoprene metabolism since squalene synthetase is a branchpoint enzyme in this pathway. It is possible that in these mutants, activities of other enzymes that utilize FPP as a substrate, such as undecaprenyl-pyrophosphate synthetase and dolichol-pyrophosphate synthetase, will undergo homeostatic changes to keep isoprenoid synthesis in balance.

EXAMPLE 5

Screen for Inhibitors of Squalene Synthetase

The cloned ERG9 gene was used to create a two-plate screen for squalene synthetase inhibitors. In this screen, an inhibitor-sensitive strain (SGY1189), which is an ERG9:HIS3 deletion haploid that carries multiple copies of pSM53, a plasmid which contains a partially detective ERG9 gene, is used. Also used is an inhibitor-resistant strain (SGY1188), which is an isogenic strain that carries multiple copies of pSM52, a plasmid which contains a normal ERG9 gene, and which possesses about 200% of the squalene synthetase activity of a wild-type cell or at least about 40 times the amount present in strain SGY1189. This screen was performed as follows:

1. *S. cerevisiae* strains SGY1188 and SGY1189 were grown overnight (20–24 hrs) in a shaker at 28° C. in Y14 broth, which is a yeast minimal medium described in Barnes, G. et al., Mol. Cell. Biol. 4, 2381–2388 (1984) supplemented with L-tryptophan (30 µg/ml), L-adenine (90 µg/ml), uracil (20 µg/ml), and ergosterol (20 µg/ml).

2. Inoculated agar was prepared for overlayer or pour plates. For strain SGY1189, 1.5% of the overnight culture and for strain SGY1188, 1.0% of the overnight culture was inoculated into molten (45°–48° C.) yeast minimal Y14 agar supplemented as above. Agar was used promptly because ergosterol is not stable at this temperature.

3. When potential natural product inhibitors were being evaluated, test microorganisms (potential inhibitor producers) were streaked and grown on 20 mm agar discs. These test blobs were placed in duplicate in empty petri dishes and overlayered with both kinds (above) of inoculated screening agar. When fermentation broths or known compounds were being evaluated, these substances were dissolved in an appropriate solvent, for example ethanol, or DMSO, applied to 12 mm filter paper discs and air-dried. The sample discs were placed on the surface of both kinds (above) of inoculated screening agar in Petri dishes. As a control, a test disc containing 50 µg nystatin (stock: 5 mg/ml in MeOH) was used; nystatin should give a 25–30 mm zone with both strains.

4. Plates were incubated at 28° C. and examined after 1.5 to 2 days for differential inhibition of growth of strain SGY1189 versus SGY1188 (an inhibitor of squalene synthetase will inhibit the growth of SGY1189 more than SGY1188 whereas a non-specific inhibitor will inhibit the growth of both strains equally).

EXAMPLE 6

Over Expression of Yeast Squalene Synthetase

To produce large quantities of squalene synthetase for enzyme purification and characterization studies, the ERG9 gene was over-expressed from a highly regulated yeast promoter. Plasmid pSM60 (FIG. 6A) was constructed using standard methods (Maniatis et al., supra) by insertion of a 2.0 kb BamH1-Sph1 fragment containing the squalene synthetase coding region and 24 bp of 5'-upstream sequences into compatible sites of the yeast expression vector pMH101 [Haffey, M. L. et al., J. Virol. 62, 4493 (1988)]. The ERG9 gene was thus fused in the proper orientation and proximity in pSM60 to place expression of squalene synthetase under the regulation of the adjacent GAL1 promoter. Yeast strain SGY879 (Squibb Genetic Yeast Collection; genotype: MATa ERG9 ura3-52 leu2-3, 112 trp1-1 his3d GAL+) was separately transformed by electroporation as described above with either pSM60 or the parent plasmid, pMH101.

Appropriate URA+ transformants were grown overnight at 28° C. in yeast minimal medium with glucose as the carbon source to an $OD_{600}$ of 0.8. Cells containing pSM60 or pMH101 were pelleted by centrifugation, washed once in water, and split into two portions, which were separately resuspended in fresh medium that contained ether 2% glucose (promoter repressing condition) or 2% galactose (promoter inducing condition) as carbon source. After further growth at 28° C. for 20 hours, glucose or galactose grown yeast were harvested by centrifugation at 8,000× g, washed once with distilled water, pelleted and frozen at −70° C. Yeast cells were thawed at 4° C. and disrupted by vortexing vigorously with glass beads in the presence of cold cell breakage buffer (0.1M $NaH_2PO_4$, pH 7.4, 4 mM $MgCl_2$, 1 mM EDTA, 10 mM 2-mercaptoethanol, 1 mM PMSF, 2 mM benzamidine, 0.1 mM EGTA, 1 µg/ml leupeptin). Cell debris was removed from the lysates at 4° C. by two sequential 10 minute centrifugations at 4000 rpm and at 10,000 rpm. The 10,000 rpm supernatants were further centrifuged at 4° C. for 1 hour at 100,000× g to produce two fractions; a supernatant corresponding to "soluble protein" and a pellet corresponding to "microsomal protein". Microsomal pellets were resuspended in a small volume (0.2 ml) of cold breakage buffer by brief homogenization (10 strokes) with a glass homogenizer. The supernatants were concentrated in spin-filtration units (Centricon-10) by centrifugation at 4° C. for 1 hour at 5500 rpm. All fractions were stored at −70° C.

Figure 6B:
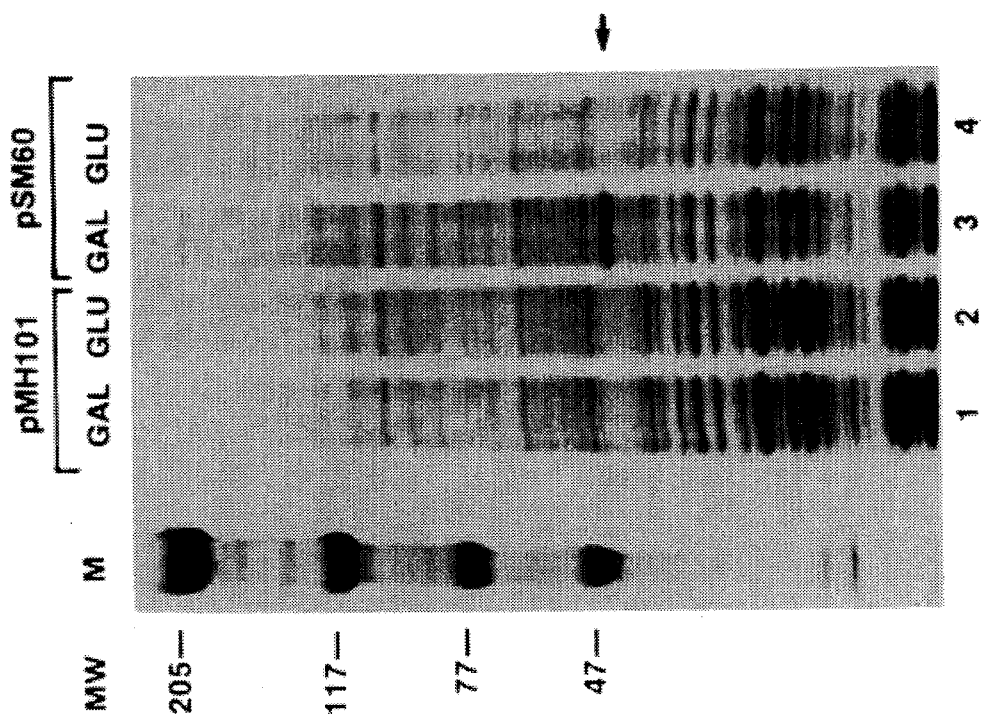
FIG. 6B shows an SDS-polyacrylamide gel of microsomal proteins extracted from galactose-induced yeast cells containing pSM60 that shows the over-production of a protein believed to be squalene synthetase.
Figure 6A:
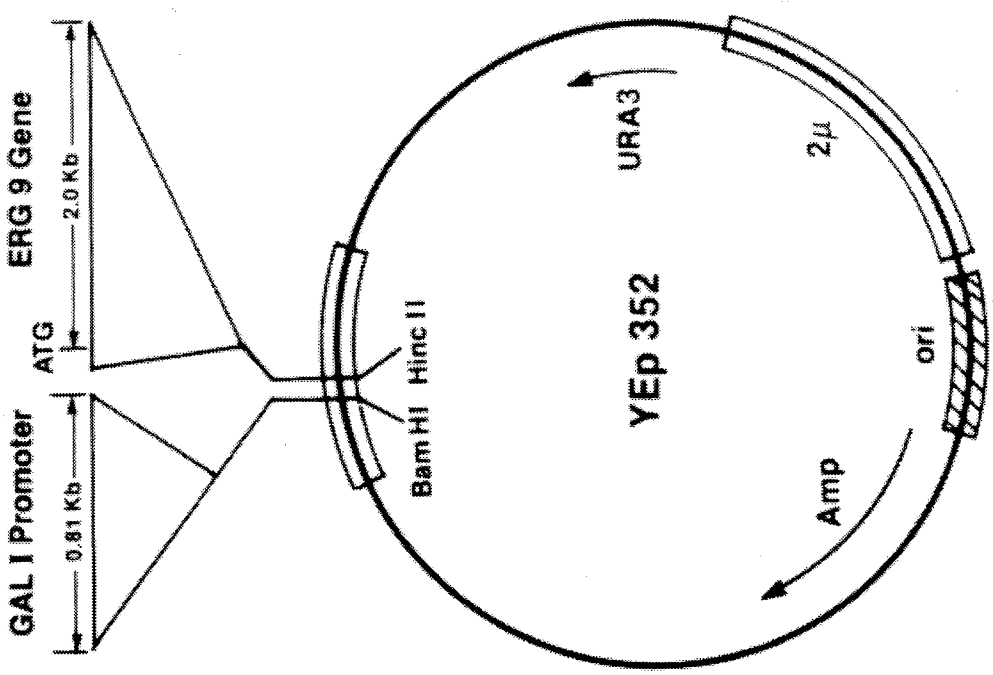
FIG. 6A shows a plasmid diagram of pSM60, which is a multicopy yeast expression vector that contains the GAL1 promoter fused to the yeast ERG9 gene so as to direct expression of this gene in a galactose-inducible manner.

Microsomal membrane fractions from the yeast above were assayed for squalene synthetase levels using the quantitative gas chromatographic assay described in S. A. Biller, et al., supra. As shown in Table 2, the specific activity of the enzyme in fractions from pSM60-transformed cells was approximately 200-fold higher in galactose versus glucose-grown cells. By contrast, enzyme levels in fractions from pMH101-transformed cells were somewhat higher in glucose-grown cells. Proteins present in these fractions were analyzed by electrophoresis on 5–20% gradient SDS-polyacrylamide gels. Equal microgram amounts of protein (15 µg/lane), as determined by dye binding assay kit (Bio-Rad), were run on SDS-PAGE gels as described in U. K. Laemmli et al., Nature 277, 680–685, (1970) and stained with Coomassie blue stain. As shown in FIG. 6B, only the fraction from pSM60-transformed cells grown on galactose contained a unique band which migrated at the same position as the ovalbumin (47 KD) molecular weight marker. The size, galactose-regulated expression, and microsomal location of this protein strongly suggest that it represents the over-expressed squalene synthetase detected by enzymatic assay above.

EXAMPLE 7

Modification of Squalene Synthetase to Produce Soluble Enzyme

Previous work on HMG CoA reductase in mammalian cells has shown that this microsomal enzyme can be converted to a soluble enzyme by deletion of its membrane-spanning domains [Gil, et al., Cell 41, 249–258 (1985)]. To determine whether the most C-terminal hydrophobic domain of squalene synthetase represented the major, or perhaps the only transmembrane domain of this protein, an appropriate truncation of the wild-type ERG9 gene was constructed using polymerase chain reaction (PCR) amplification.

As a template for the PCR reaction, a 1.5 kb Acc1 fragment containing the entire ERG9 gene was purified from pSM51 (FIG. 1). After restriction enzyme digestion, agarose gel electrophoresis and fragment purification using GeneClean (Bio 101, LaJolla, Calif.), the template DNA was suspended in TE buffer [10 mM Tris-HCl, pH 8.0, 1 mM EDTA] at a concentration of 100 µg/ml. PCR reaction mixtures contained 100 ng of template DNA, 1 µg each of sense and antisense amplimers, 200 µM each of ATP, CTP, GTP and TTP, and 2.5 units Taq DNA polymerase in a total volume of 0.1 ml buffer A [50 mM KCl, 1.5 mM $MgCl_2$, 0.1% gelatin (w/v) and 10 mM Tris-HCl, pH 8.3]. The sense amplimer used was GWR#24 that had the sequence 5'-GCAGATCTCACACAATGGGAAAGCTATTACAATT-3' and the anti-sense amplimer used was GWR#2 that had the sequence 5'-GTCTAGATCTTGTACTCTTCTTCTTGT-TGGGTTG-3'.

The PCR amplification was performed using the following thermal cycling program:

Segment 1—heat samples to 94° C. in no less than 30 seconds;

Segment 2—incubate samples at 94° C. for 1 minute;

Segment 3—cool samples to 52° C. in no less than 1 minute;

Segment 4—incubate samples at 52° C. for 2 minutes;

Segment 5—heat samples to 72° C. in no less than 30 seconds;

Segment 6—incubate samples at 72° C. for 5 minutes.

This thermal cycle consisting of segments 1–6 was repeated 35 times with an automatic 10 second extension of segment 6 after each cycle. After finishing with all 35 cycles, the samples were incubated an additional 7 minutes at 72° C. and then stored at 4° C. for further analysis. The amplified 1284 bp DNA fragment was isolated after agarose gel electrophoresis and purified using GeneClean. This fragment was digested with the restriction enzymes Bgl2 and Xba1, to produce "sticky ends" suitable for cloning, then phenol/chloroform extracted and ethanol precipitated according to standard procedures (Maniatis et al., supra). The Bgl2-Xba1 digest fragment was ligated into the BamH1-Xba1 digested vector pSM64 to produce the plasmid pSM80. In order to prepare pSM64, vector pSM63 was first derived from pSM60 by removing a 2.02 kb BamHI-XbaI fragment and inserting a 21 bp BamHI-XbaI oligonucleotide that had the sequence 5'GATCCGTATTGAAG-GTCGACT-3'. pSM64 was derived from pSM63 by removing a 10 bp XbaI-PstI fragment and inserting a 138 bp XbaI-NsiI fragment generated from a 335 bp PCR product produced exactly as described above except utilizing GWR #21 (5'-GGTCTAGAGTCTGCGCCAAATAACAT-AAACAAAC-#") and GWR #1 (5'-GTCTAGATCTA-GAGTTGCCTAAGACTTTGCGTCG-3') as sense and antisense amplimers, respectively. Plasmid pSM80 was nearly identical to the ERG9 overexpression vector pSM60 (described in example 6), except that the ERG9 coding region of pSM80 was missing 24 codons at the 3'-end of the gene. The PCR reaction also introduced an in-frame translational stop codon ("TAG" in the Xba1 site) after lysine-420, to ensure termination of the ERG9 coding region of pSM80 at this point.

To determine the characteristics of the modified squalene synthetase protein encoded by pSM80, this plasmid and pSM60 (encoding wild-type protein) were transformed into yeast strain SGY879 PEP4::HIS3 by standard methods. This strain had the genotype (MATa ERG9 ura3-52 leu2-3, 112 trp1-1 PEP4::HIS3 GAL+). It was capable of GAL promoter induction and was also reduced in intracellular proteases due to the PEP4 deletion. Transformants were selected and propagated as URA+ cells on yeast minimal medium with glucose as carbon source. Galactose induction of yeast cells transformed with either pSM60 or pSM80 was accomplished exactly as described earlier (example 6).

Figure 7:
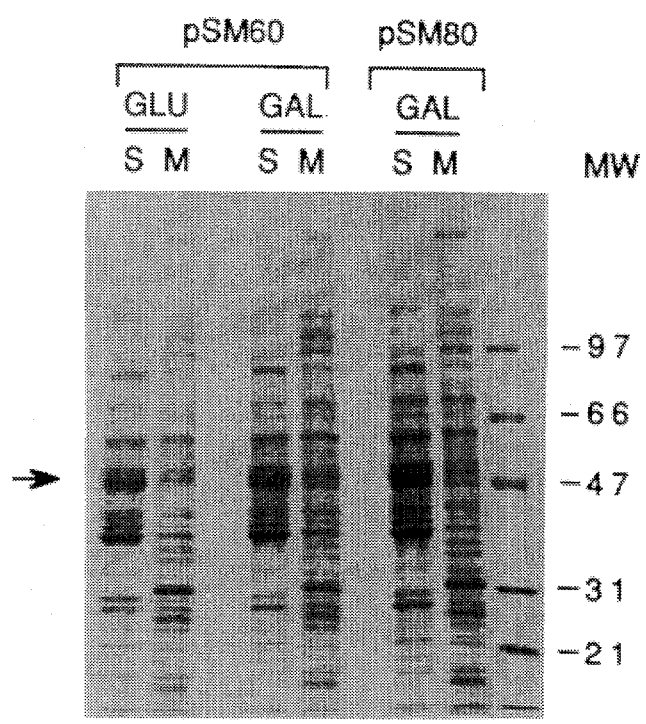
FIG. 7 shows an SDS-polyacrylamide gel of microsomal and soluble proteins extracted from galactose-induced yeast cells containing either pSM60 or pSM80 that demonstrates the production of a protein believed to be soluble squalene synthetase in pSM80-containing cells.

Squalene synthetase protein in the yeast fractions was analyzed by electrophoresis on 5–20% gradient SDS-polyacrylamide gels as described in Example 6. Equal microgram amounts of protein (15 µg/lane), as determined by dye binding assay kit (Bio-Rad), were loaded and run on SDS-PAGE gels as described (Example 6) and stained with Coomassie blue stain. As shown in FIG. 7, neither soluble nor microsomal fractions from pSM60-transformed cells grown in glucose medium produced a band of 47 K daltons. pSM60-transformed cells grown in galactose produced a strong band of this size in microsomal but not in soluble fractions. As described in Example 6, there is good evidence that this band represents over-expressed, membrane-bound squalene synthetase. Significantly, both soluble and microsomal fractions from pSM80-transformed cells grown in galactose produced bands of approximately 47K daltons. Gel densitometry indicated that about half of the modified squalene synthetase expressed from pSM80 was associated with the soluble fraction. Because the pSM60 protein should be homogeneous, the portion remaining microsomal may be membrane associated but not tightly bound. The predicted sizes of the pSM60 and pSM80-encoded proteins were 51,753 and 49,890, respectively, but both migrated as 47K dalton proteins on SDS-PAGE gels.

To determine whether the soluble squalene synthetase still retained enzymatic activity, biochemical assays were done using the various protein fractions. As shown in Table 3, activity in pSM60 galactose-grown cells distributed entirely (99.7%) into the microsomal fraction, whereas in pSM80 cells 13% of the activity was found in the soluble fraction. These results indicated that the soluble pSM80 enzyme was still active, but not as active as the protein associated with membrane. These experiments demonstrate that removal of the last 24 amino acids from squalene synthetase convert it from an intrinsic membrane protein to a soluble protein and thereby prove that the fourth hydrophobic domain is the only transmembrane domain of this protein. Over-production of this soluble active form of squalene synthetase (from pSM80) should greatly facilitate the purification and characterization of this interesting enzyme.

EXAMPLE 8

Cloning and Characterization of Human and *Schizosaccharomyces pombe* Squalene Synthetase cDNAs I. Materials and Methods A. Strains and cell lines The following strains of *Saccharomyces cerevisiae* were used in this study: W3031A (MTAa) and W3031B (MATα) both (ERG9 leu23, 112 ade21 ura3-1 trp1-1 his3-11,15) were from R. Rothstein (Columbia University); SGY879 (MATα ERG9 leu2-3, 112 ura3-52 his3-11,15 trp1-1) and SGY1202 (isogenic to SGY879 but ERG9::HIS3) were constructed in our laboratory. *Schizosaccharomyces pombe* strain SGY131 (h-ERG9) was also used.

*Escherichia coli* strains used were DH5α [F-Δ 80dlacZ M15, endA1, recA1, hsdR17, supE44, thi-1, gryA, relA1, Δ(lacZYA-argF)U169] and DH5αMCR [same as DH5α pluc mcrA, mcrB, mrr] from Bethesda Research Laboratories, Gaithersburg, Md.

Normal human fibroblast cells designated CRL1508 were obtained from the ATCC and transformed with SV40 virus to derive a permanent cell line called CRL1508T that was used in the RNA regulation studies.

B. Plasmids and expression libraries pDB20 (Fikes, et al. Nature 346:291 (1990)) is a high copy number, autonomously replicating *Saccharomyces cerevisiae—Escherichia coli* shuttle vector which confers ampicillin resistance to *Escherichia coli* and uracil prototrophy to ura3 yeast. It contains a *Saccharomyces cerevisiae* ADH1 promoter fragment suitable for expression of heterologous cDNA's. Expression libraries bearing HeLa cell or *Schizosaccharomyces pombe* cDNAs were obtained from L. Guarente (Harvard University) (Fikes, et al. Nature 346:291 (1990)); both contained polydT-primed cDNAs inserted at a unique BstXI site of pDB20 and represented pools of as least 2×10$^6$ independent clones.

Media, growth and transformation conditions

*Saccharomyces cerevisiae* strains were grown at 28° C. in either YEPD (Tsay, Y. H., et al., Mol. Cell. Biol. 11:620 (1991)) or YPD-E (YPD supplemented with 20 μg/ml ergosterol) medium to obtain cells for transformations. Strains harboring vectors that contained the URA3 gene were grown in YM or YM-E (ergosterol-supplemented YM) synthetic medium lacking uracil ((Tsay, Y. H. et al., Mol. Cell. Biol. 11:620 (1991)). Yeast were grown in YPD or YM aerobically and in YPD-E or YM-E anaerobically. Transformation of *Saccharomyces cerevisiae* strains was by the modified lithium acetate method (Schiestt, R. H., and Gietz, R. D., Yeast Genetics and Molecular Biology Meeting Abstracts, p. 106A (1991)). Ura$^+$ transformants were selected on YM-E agar plates after 5 days of growth in an anaerobic chamber at 28° C.

D. Screening of cDNA libraries for functional complementation

HeLa cell and *Schizosaccharomyces pombe* cDNA libraries in the vector pDB20 were used to transform the ERG9::HIS3 strain SGY1202 to uracil prototrophy. Ura$^+$ plasmid transformants obtained after anaerobic selection were harvested from the surface of plates by manual suspension in YM. Transformants were pooled, replated onto YM agar plates and grown aerobically to screen for transformants that were ergosterol prototrophs. DNA from prototrophic colonies was used to transform *Escherichia coli* to ampicillin resistance.

E. PCR-based screening of a human cDNA library

Protein sequences that were identical in *S. cerevisiae* and *S. pombe* squalene synthetases were used to design ambiguous primers for PCR amplification of an approximately 400 bp fragment. The 5' oligonucleotide primer was 5'-GGAGTAYTGYCAYTAYGTIGCNGGICTNGTNGG-3' and the 3' primer was 5'-GGATGCATGCCATIACYTGNGGNATNGCXCAXAA-3', where X is G, A mixed; Y is C, T mixed; N is G, A, C, T mixed and I is inosine. In PCR reactions, 400 ng of each primer were added to 2 μg of HeLa cell library DNA in a total volume of 0.1 ml. After 35 cycles of amplification, a PCR product was purified by agarose gel electroporesis and subcloned into pUC18 to create pET129, from which insert DNA was sequenced.

Sequences at the 5'-end of the human squalene synthetase coding region were obtained from the HeLa cell library DNA using the conditions described above except that the 5' oligonucleotide primer corresponded to the pDB20 vector sequence: 5'-CCAATGGCGAAGAAGTCCAAAGCTT-3' and the 3' primer corresponded to sequences adjacent to human squalene synthetase domain 2 (FIG. 4): 5'-GCGGTCGACCGCCAGTCTGGTTGGTAAAGGAAAGAGTG-3'. A PCR product of approximately 390 bp was purified, subcloned into pBluescript to create pET140, and sequenced.

F. Screening of bacteriophage λ cDNA library

A human adult liver cDNA library constructed in a lambda Uni-Zap XR vector was obtained from Stratagene (LaJolla, Calif.). The library represented a pool of 2.0×10$^6$ recombinant plaques and was screened using standard hybridization cloning procedures (Maniatis, et al., supra). The 400 bp PCR fragment (from HeLa cells) present in pET129 was radiolabeled by random priming and used as a DNA probe of library filters under stringent hybridization conditions. Positive clones from the library were purified and converted into pBluescript phagemids by superinfection of *Escherichia coli* with lambda clones and f1 helper bacteriophage. Phagemid insert DNAs were sequenced.

G. DNA sequence analysis

The DNA sequences of human and *Schizosaccharomyces pombe* ERG9 cDNAs were determined from pUC18 or pBluescript subclones using the dideoxynucleotide chain termination method (Sanger, et al., supra). Sequencing reactions were performed using Gene-Amp Taq polymerase and fluorescent primers following the Perkin-Elmer protocol and products were read on an Applied Biosystems 373A DNA sequencer. The sequence of both coding and noncoding strands of all cDNA clones were determined. Sequence data were assembled and analyzed using Intelligenetics and GeneWorks software. Searches for DNA and protein sequence homologies to squalene synthetase were conducted using NBRF/GenBank (release 63.0), PIR (release 23.0) and Swiss-Prot (release 13.0) data bases.

H. Northern blot analyses

*Saccharomyces cerevisiae* strain SGY879 and *Schizosaccharomyces pombe* strain SGY131 were grown to stationary phase cultures in YM medium, then inoculated at low cell density into fresh YM that contained either no additive or test compound (lovastatin). Cultures were grown for 16–20 hours until all had achieved a density of approximately $1 \times 10^7$ cells per milliliter. Cells were pelleted, washed with cold phosphate buffered saline and frozen as aliquots at $-70°$ C. Total RNA was extracted from cells using the glass bead/phenol procedure (Kohrer, K. and Domdey, H. (1991) In Guide to Yeast Genetics and Molecular Biology, Guthrie, C., and Fink, G. R., eds, pp. 398–405, Academic Press, New York), then fractionated on agarose gels containing 50% formaldehyde. After blotting to nitrocellulose membranes, RNAs were hybridized with an appropriate radiolabeled *Saccharomyces cerevisiae* or *Schizosaccharomyces pombe* ERG9 DNA probe and exposed to X-ray film. Hybridization was at 42° C. for 16 hours in 50% formamide, 0.25M $NaH_2PO_4$, pH 7.2, 0.25M NaCl, 1 mM EDTA, 7% SDS and 100 μg/ml denatured salmon sperm DNA. The human fibroblast cell line 1508T was maintained in minimum essential medium (MEM) containing 10% FCS. For RNA expression studies, cells at approximately 70% confluence were washed in MEM alone and then shifted to MEM containing 5% calf lipoprotein deficient serum (CLPDS) with or without 1 μM lovastatin. After 48 hours, cell monolayers were washed twice in TBS, scraped and pelleted by centrifugation. Total RNA was prepared by the guanidiniumisothiocyanate method and polyA+ RNA was purified from total RNA by polydT cellulose chromatography. Gel fractionation, transfer to membranes and probing of RNAs were all done essentially as described above, except that sample data was normalized to RNA signals from ribosomal LS30 (Wiedemann, L. M., et al., Mol. Cell. Biol. 4: 2518 (1984).

I. Construction of yeast and mammalian expression vectors

The vector pCM13 used for expression human squalene synthetase in yeast was constructed in a three-piece ligation of a 7.2 kb NotI-XhoI fragment of pET125, a 0.3 kb NotI-SstI fragment of pET140, and a 1.1 kb SstI-XhoI fragment of pET137. The human/*S. cerevisiae* ERG9 chimera of plasmid pCM14 was made by ligation of a 6.0 kb PstI-NcoI fragment of pCM13, a 0.25 kb PstI-MscI fragment of pET137 and a 2.0 kb fragment of pSM60. The vector pGR66 used for expression of human squalene synthetase in COS7 cells was constructed by cloning a 1.4 kb HindIII-XhoI fragment from pCM13 into a 4.7 kb HindIII-SalI fragment from pCMV5 (Andersson, S. et al., J. Biol. Chem. 264:8222 (1989)).

J. Transient expression in COS-7 cells

The human squalene synthetase expression plasmid, pGR66, was transfected into COS-7 cells by electroporation using a Bio-Rad Gene Pulser (model 1652076) according to the manufacturer's recommendations. Approximately $3 \times 10^6$ cells were transfected with 10–30 μg of the plasmid and plated onto 100 mm dishes. Following 40 hours of expression in MEM+10% FCS, cell microsomal membranes were prepared and assayed for enzyme activity.

K. Microsomal extracts and squalene synthetase activity

Preparation of crude "microsomal membranes" from quick-frozen fungal cells and human cells was as previously described. Squalene synthetase activity in these samples was measured using a radiochemical assay (Poulter, C. D. and Rilling, H. C. (1981) in Biosynthesis of Isoprenoid Compounds, Porter, J. W., and Spurgeon, S. L., eds., pp. 413–442, Willey, New York).

II. Results

A. Isolation and expression of a cDNA clone encoding squalene synthetase from *Schizosaccharomyces pombe*

DNA fragments bearing the *Schizosaccharomyces pombe* ERG9 coding region were isolated from a cDNA library by phenotypic complementation of a *Saccharomyces cerevisiae* ERG9 deletion mutant (SGY1202). A total of $1 \times 10^6$ library transformants of this squalene synthetase-null strain were screened to identify recombinant plasmids that could convert the strain to ergosterol prototrophy. From 15 prototrophs, a single plasmid designated pET125, that contained a DNA insert of 1.5 kb, was isolated. Cells bearing pET125 possessed approximately five times the level of squalene synthetase found in wild-type *Saccharomyces cerevisiae* strains. These experiments demonstrated that pET125 bore a functional ERG9 gene that could be expressed from the ADH1 promoter element present on the pDB20 vector. Restriction enzyme analysis showed that the insert of pET125 had a different restriction map that did the *S. cerevisiae* ERG9 gene.

B. Isolation and expression of a cDNA clone encoding squalene synthetase from human cells Initial attempts to isolate a cDNA encoding human squalene synthetase followed the same strategy used for the *Schizosaccharomyces pombe* clone, namely screening of a cDNA expression library in SGY1202. Over $2 \times 10^6$ plasmid transformants of SGY1202 with a HeLa cell library were screened without identifying any ergosterol prototrophs. When the sequence of the *Schizosaccharomyces pombe* squalene synthetase became known, highly conserved regions of the *Schizosaccharomyces pombe* and *Saccharomyces cerevisiae* proteins (domains 3 and 5, described below) were used to design two degenerate olignucleotide primers for polymerase chain-reaction (PCR) amplification. With these primers, a 381 bp fragment was amplified from the HeLa cell cDNA library above and its nucleotide sequence was found to encode a polypeptide homologous to ones present in the two fungal enzymes. This PCR fragment was used as probe to obtain human cDNAs from a library in bacteriophage lambda. From approximately $2 \times 10^5$ plaques, twelve hybridization-positive clones were purified, bearing inserts of 1.2, 1.5 and 1.8 kb in size. DNA sequencing showed that all these clones were incomplete, so PCR was used to obtain a further 220 bp of 5' sequences by amplification from the HeLa cell library (see Materials and Methods).

Ligation of the 220 bp 5'-fragment to the 1.2 kb cDNA produced a longer 1.4 kb coding region that was directionally subcloned into the yeast vector pDB20 to create plasmid pCM13. This plasmid did not convert SGY1202 to ergosterol prototrophy, however a similar plasmid (pCM14) bearing a human/*S. cerevisiae* chimeric gene (see Materials and Methods) did complement the strain and produced detectable microsomal enzyme. When the 1.4 kb human coding region was transiently expressed in COS-7 cells using the CMV promoter of pGR66, a 73-fold increase in squalene synthetase activity over levels in control cells was observed. Thus, the 1.4 kb coding region encodes a functional enzyme and the failure of pCM13 to complement SG1202 likely reflects a problem with expression of the gene in yeast.

C. *Schizosaccharomyces pombe* and human ERG9 DNA Sequences

A single ORF beginning with a methionine codon was detected in pET125, 30 bp downstream of the BstX1 insertion site on the vector. The pET125 ORF predicted a protein of 460 amino acids with a $M_r$ of 53,427, a size similar to that of the *Saccharomyces cerevisiae* squalene synthetase (See above). Likewise, on pCM13, 40 bp from the insertion site a continuous ORF of 417 amino acids was identified, encoding a protein with a calculated molecular mass of 48,118 kDa. The complete nucleotide and deduced primary sequence of *Schizosaccharomyces pombe* (FIG. 8) and human squalene synthetase (FIG. 9) ORF's are shown. At the nucleotide level, conservation between the *Schizosaccharomyces pombe* and human ORF's is 45%, between the *Saccharomyces cerevisiae* and human ORF's it is 48%, and between the two fungal ORF's it is 47%. The 1.8 kb, but not the 1.2 or 1.5 kb human cDNA contained canonical polyadenylation signals (AATAAA) 600 and 700 bp downstream of the squalene synthetase stop codon. The *Schizosaccharomyces pombe* clone lacked such a signal in its 3'-untranslated region, suggesting that this cDNA may have been formed by spurious poly-dT priming 5' of the bona fide polyadenylation site.

D. Squalene Synthetase Protein Comparisons

Figure 11:
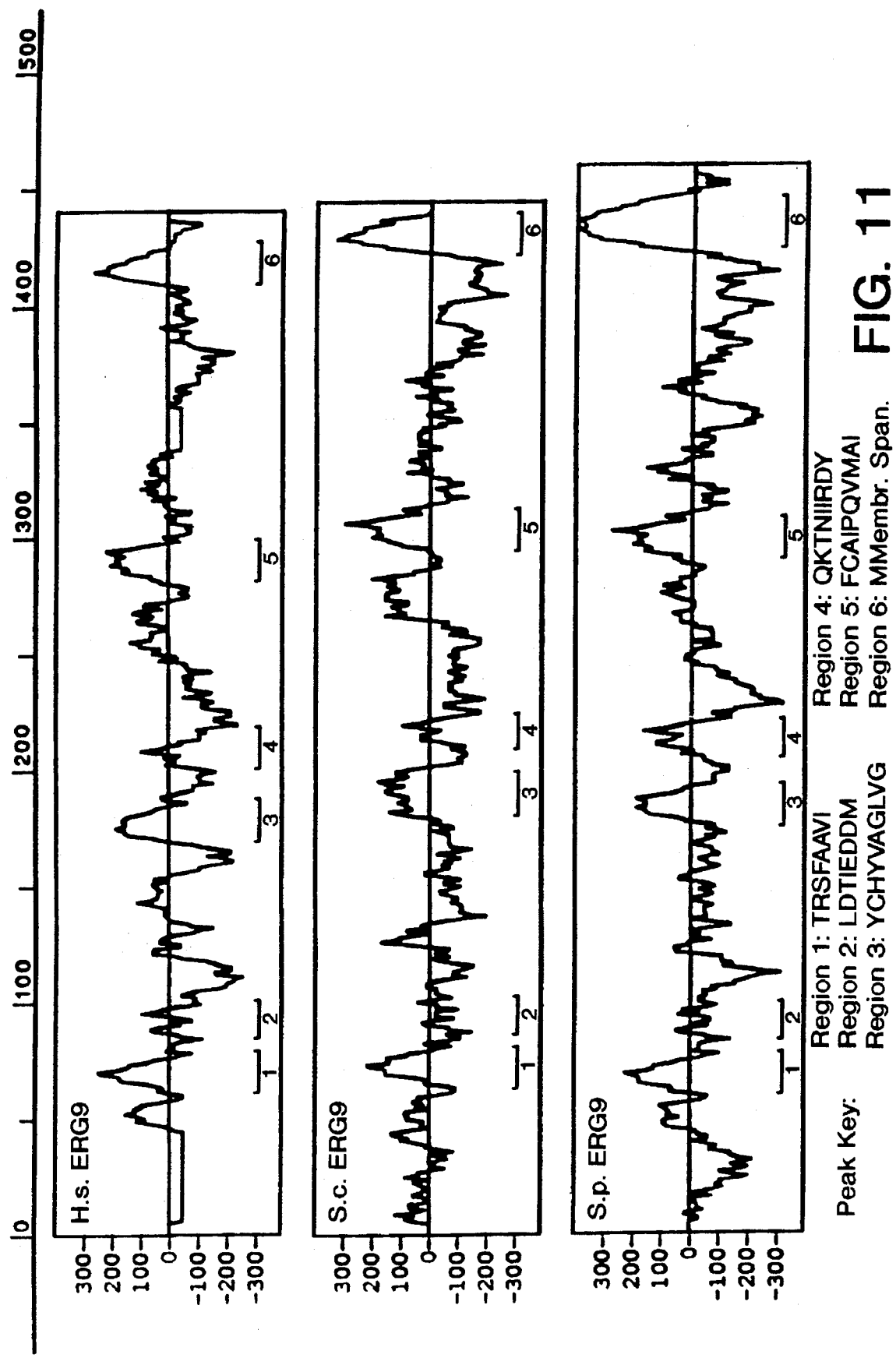
FIG. 11 shows hydrophobicity plots for human (H.S.), *Saccharomyces cerevisiae* (S.c.) and *Schizosaccharomyces pombe* (S.p.) squalene synthetases.

A comparison of amino acid sequences of the three squalene synthetases is shown in FIG. 10. Conservation between any two of the three proteins is only 36% for identical residues and approximately 51% for similar plus identical residues. Other proteins in the Swiss-Prot protein database which bear limited homology to squalene synthetases (Ashloy, M. N. et al., J. Biol. Chem. 267, 4128 (1992)) use similar prenyl diphosphate substrates and have at least one copy of an aspartate-rich motif with the consensus sequence: (I/L/M)GLAFQ(T/L)LDDI(L/R) D(D/V)XG(D/S)TAAL(G/R)K. This motif has been proposed to represent a binding site for the $Mg^{+2}$/diphosphate moiety of the substrates. In the squalene synthetases, two regions bear this motif (FIG. 10 and FIG. 11; domains 2 and 4) and each contains a pair of aspartate residues; these four aspartates are the only conserved ones in all squalene and phytoene synthetases. Interestingly, both domains bearing the motif are bounded on their N-terminal sides by extended hydrophic domains (FIG. 11, domains 1 and 3).

Previous hydropathy analyses of the *Saccharomyces cerevisiae* squalene synthetase identified four regions of the protein which could serve as membrane-associated helices. Deletion of the most C-terminal hydrophobic region (FIG. 11, domain 6), converts the *Saccharomyces cerevisiae* protein from a membrane-bound to a soluble enzyme (see above), establishing this as the only transmembrane domain of the protein. The human and *Schizosaccharomyces pombe* proteins also have hydrophobic α-helical regions near their C-termini (FIG. 11). Primary sequence conservation is poor in these regions (FIG. 10), as would be expected if they represent simple membrane-spanning domains. Like the *Saccharomyces cerevisiae* protein, neither the human nor the *Schizosaccharomyces pombe* protein contains a proposed ER membrane-retention motif.

Other hydrophobic regions in the squalene synthetases are strikingly different from the C-terminal region because they contain highly conserved sequences of the proteins. Domain 3 (FIG. 10) is unique among squalene synthetase sequences in having a primary and secondary structure suggestive of a binding pocket of NAD(P)H. It contains the sequence, "VAGLVGXG", and resembles the highly conserved sequence, "XhXhGXGXXG", which forms a critical loop in the β-α-β dinucleotide binding fold of numerous proteins. Curiously, domain 3 sequences are partially conserved among the phytoene synthetases, which do not require a nucleotide cofactor for catalysis (FIG. 10). The hydrophobic sequence of domain 5 is not present in any other databank protein.

A fourth hydrophobic region identified in the *Saccharomyces cerevisiae* squalene synthetase (FIG. 11, residues 265 to 285) is not conserved as a major hydrophobic domain in the other squalene synthetases. A conserved hydrophilic region just proximal to the likely membrane-spanning domain contains a "PEST" site in the *Saccharomyces cerevisiae* protein, but not in the others. Of numerous potential kinase sites present in the squalene synthetase proteins, only ones for tyrosine kinase (FIG. 10, Tyr; near position 345) and casein kinase II phosphorylation (FIG. 10, Thr; near position 77) are conserved.

Enzyme inactivation studies using the arginine-specific reagent, hydroxyphenylglyoxal, have implicated arginine residues in reactions catalyzed by squalene and phytoene synthetases. Arginine residues could participate in the binding of substrate diphosphates, so it may be significant that the only arginines common to all squalene and phytoene synthetases are in pairs, close to paired aspartate residues (FIG. 10).

E. Size and Regulation of squalene synthetase mRNAs

To determine the size of squalene synthetase transcripts, total or poly(A)$^+$ RNA from wild-type yeast strains and a transformed human fibroblast cell line, CRL1508T, were examined by hybridization using the appropriate species-specific probes. Radiolabeled fragments from pSM54 and pET123 each identified a single transcript of approximately 1.8 kb from *Saccharomyces cerevisiae* or *Schizosaccharomyces pombe* RNA, respectively. By contrast, a human probe from pET137 identified transcripts from CRL1508T cells of 1.6, 1.9 and 2.25 kb, whose relative abundance varied according to the ratio, 1/3/1. These sizes were similar to those of the three human liver cDNA clones, suggesting that the three transcripts may represent RNAs that vary in the length of their 3'-ends.

Levels of many of the enzymes of isoprene and sterol synthesis are regulated by treatments which affect the requirement of cells for endogenous synthesis of sterols. To examine regulation in mammalian cells, Northern blot analysis was performed using poly(A)$^+$ mRNA from CRL 1508T cells grown for 48 hours in medium containing excess (DMEM+10% FBS) or limiting CLPDS+5% FBS) amounts of cholesterol. Normalized to L30 RNA, squalene synthetase mRNA levels in serum-deprived cells were 1.3-fold higher than levels in control cells. When cells were grown in medium that contained limiting cholesterol and 10 µM lovastatin (a competitive inhibitor of HMG-CoA reductase) for 48 hours, enzyme-specific mRNA levels rose 3.2-fold above those in control cells (DMEM+10% FBS). The relative abundance of the three transcripts did not shift in response to the changes in cellular growth conditions.

All publications and patents referred to in the present application are incorporated herein by reference to the same extent as if each individual publication or patent was specifically and individually indicated to be incorporated by reference.

TABLE 1

Segregation of Genetic Markers in SGY1161 Disruption Diploids

| Diploid Genotype (Presumed)[a] | # Tetrads Examined | Spore Phenotype[b] | | |
|---|---|---|---|---|
| | | ERG9:erg9 | LEU2:leu2 | HIS3:his3 |
| ERG9/ERG9 | 22 | 4:0 | 0:4 | 0:4 |
| ERG9/ERG9::LEU2 | 23 | 2:2 | 2:2 | 0:4 |
| ERG9/ERG9::HIS3 | 11 | 2:2 | 0:4 | 2:2 |
| SGY1161 MATa ERG9 his3-11 leu2-3,112 trp1-1 ura3-1 ade2-1 can1-100 | | | | |
| MATα ERG9 his3-11 leu2-3,112 trp1-1 ura3-1 ade2-1 can1-100 | | | | |

[a]The wild-type diploid strain SGY1161 (ERG9/ERG9) was disrupted in an ERG9 allele by integration of a linear ERG9::HIS3 or ERG9::LEU2 disruption fragment from pET105 or pET106, respectively.
[b]Complete tetrads were recovered by anaerobic growth on YEPD medium supplemented with ergosterol; Spores were tested for ergosterol prototrophy (ERG) or auxotrophy (erg) by checking their viability in the absence of ergosterol.

TABLE 2

Squalene Synthetase Levels In Yeast Microsomes

| Plasmid | Construct | Medium | Amt. Squal.[a] | Synth. Act.[b] |
|---|---|---|---|---|
| pMH101 | GAL1-XX | GLU | 0.160 | 0.100 |
| pMH101 | GAL1-XX | GAL | 0.030 | 0.020 |
| pSM60 | GAL1-E9 | GLU | 0.190 | 0.070 |
| pSM60 | GAL1-E9 | GAL | 0.220 | 14.000 |

[a]Amount Squalene = nmol squalene/100 mg protein
[b]Squalene Synthetase Act. = nmol/min/mg protein

TABLE 3

Squalene Synthetase Levels In pSM80 Cell Fractions

| Plasmid | Construct[a] | Medium | Fraction | Synth. Act.[b] |
|---|---|---|---|---|
| pSM60 | GAL1-E9wt | GLU | soluble | 0.14 |
| pSM60 | GAL1-E9wt | GLU | microsomal | 0.38 |
| pSM60 | GAL1-E9wt | GAL | soluble | 0.08 |
| pSM60 | GAL1-E9wt | GAL | microsomal | 25.00 |
| pSM80 | GAL1-E9td | GAL | soluble | 0.54 |
| pSM80 | GAL1-E9td | GAL | microsomal | 3.50 |

[a]E9wt: ERG9 wild-type; E9td: ERG9 C-terminal deletion
[b]Squalene Synthetase Specific Act. = nmol/min/mg protein

What is claimed is:

1. An isolated nucleic acid molecule comprising a sequence coding for the amino acid sequence of FIGS. 2, 8, or 9 (SEQ ID NOS. 2, 4, or 6).

2. The nucleic acid molecule according to claim 1 which is a DNA molecule and wherein the nucleic acid sequence is a DNA sequence.

3. The DNA molecule according to claim 2 wherein the DNA sequence coding for the carboxy terminal transmembrane amino acid sequence has been deleted.

4. An isolated nucleic acid molecule having a sequence coding for the amino acid sequence of FIGS. 2, 8 or 9 (SEQ. ID. NOS. 2, 4 or 6).

5. The nucleic acid molecule according to claim 4 which is a DNA molecule and the nucleic acid sequence is DNA sequence.

6. The DNA molecule according to claim 5 wherein the DNA sequence coding for the carboxy terminal transmembrane amino acid sequence has been deleted.

7. A DNA molecule having a sequence coding for amino acid residues 1–420 in FIG. 2 (SEQ. ID. NO. 2).

8. A DNA molecule having the nucleotide sequence shown in FIGS. 2, 8 or 9 (SEQ. ID. NOS. 1, 3, or 5).

9. An isolated DNA molecule having a DNA sequence which is complementary to the DNA sequence according to claim 8.

10. An expression vector comprising a DNA sequence coding for the amino acid sequence of FIGS. 2, 8, or 9 (SEQ. ID. NOS. 2, 4, or 6).

11. The expression vector according to claim 10 wherein the DNA sequence codes for the amino acid sequence of FIGS. 2, 8, or 9 (SEQ. ID. NOS. 2, 4, or 6) in which the carboxy terminal transmembrane sequence has been deleted.

12. The expression vector according to claim 10 comprising one or more control DNA sequences capable of directing the replication and/or the expression of and operatively linked to the DNA sequence coding for the amino acid sequence of FIGS. 2, 8, or 9 (SEQ. ID. NOS. 2, 4, or 6).

13. The expression vector according to claim 10 wherein the DNA sequence has the nucleotide sequence shown in FIGS. 2, 8, or 9 (SEQ. ID. NOS. 1, 3, or 5).

14. A prokaryotic or eukaryotic host cell containing the expression vector according to claim 10.

15. The host cell according to claim 14 wherein the host cell is a yeast cell.

16. A method for producing a polypeptide molecule which comprises squalene synthetase comprising culturing a host cell according to claim 14 under conditions permitting expression of the polypeptide.

17. An expression vector comprising a DNA sequence coding for amino acid residues 1–420 in FIG. 2 (SEQ. ID. NO. 2).

18. An expression vector comprising the DNA sequence shown in FIGS. 2, 8, or 9 (SEQ. ID. NOS. 1, 3, or 5).

19. The expression vector according to claim 18 having the sequence of pSM60.

20. A prokaryotic or eukaryotic host cell containing the expression vector according to claims 11, 17, 12, 18, 13, or 19.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 2054 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 368..1699

( x i ) SEQUENCE DESCRIPTION: SEQ ID NO:1:

```
TCTAGAGACC  CTGCGAGCGT  GTCCCGGTGG  GTTCTGGGAG  CTCTAACTCC  GCAGGAACTA     60

CAAACCTTGC  TTACACAGAG  TGAACCTGCT  GCCTGGCGTG  CTCTGACTCA  GTACATTTCA    120

TAGCCCATCT  TCAACAACAA  TACCGACTTA  CCATCCTATT  TGCTTTGCCC  TTTTTCTTTT    180

CCACTGCACT  TTGCATCGGA  AGGCGTTATC  GGTTTTGGGT  TTAGTGCCTA  AACGAGCAGC    240

GAGAACACGA  CCACGGGCTA  TATAAATGGA  AAGTTAGGAC  AGGGGCAAAG  AATAAGAGCA    300

CAGAAGAAGA  GAAAGACGA   AGAGCAGAAG  CGGAAAACGT  ATACACGTCA  CATATCACAC    360

ACACACA  ATG  GGA  AAG  CTA  TTA  CAA  TTG  GCA  TTG  CAT  CCG  GTC  GAG  ATG    409
         Met  Gly  Lys  Leu  Leu  Gln  Leu  Ala  Leu  His  Pro  Val  Glu  Met
         1              5                        10

AAG  GCA  GCT  TTG  AAG  CTG  AAG  TTT  TGC  AGA  ACA  CCG  CTA  TTC  TCC  ATC    457
Lys  Ala  Ala  Leu  Lys  Leu  Lys  Phe  Cys  Arg  Thr  Pro  Leu  Phe  Ser  Ile
15                  20                       25                            30

TAT  GAT  CAG  TCC  ACG  TCT  CCA  TAT  CTC  TTG  CAC  TGT  TTC  GAA  CTG  TTG    505
Tyr  Asp  Gln  Ser  Thr  Ser  Pro  Tyr  Leu  Leu  His  Cys  Phe  Glu  Leu  Leu
                    35                       40                       45

AAC  TTG  ACC  TCC  AGA  TCG  TTT  GCT  GCT  GTG  ATC  AGA  GAG  CTG  CAT  CCA    553
Asn  Leu  Thr  Ser  Arg  Ser  Phe  Ala  Ala  Val  Ile  Arg  Glu  Leu  His  Pro
              50                       55                       60

GAA  TTG  AGA  AAC  TGT  GTT  ACT  CTC  TTT  TAT  TTG  ATT  TTA  AGG  GCT  TTG    601
Glu  Leu  Arg  Asn  Cys  Val  Thr  Leu  Phe  Tyr  Leu  Ile  Leu  Arg  Ala  Leu
         65                       70                       75

GAT  ACC  ATC  GAA  GAC  GAT  ATG  TCC  ATC  GAA  CAC  GAT  TTG  AAA  ATT  GAC    649
Asp  Thr  Ile  Glu  Asp  Asp  Met  Ser  Ile  Glu  His  Asp  Leu  Lys  Ile  Asp
     80                       85                       90

TTG  TTG  CGT  CAC  TTC  CAC  GAG  AAA  TTG  TTG  TTA  ACT  AAA  TGG  AGT  TTC    697
Leu  Leu  Arg  His  Phe  His  Glu  Lys  Leu  Leu  Leu  Thr  Lys  Trp  Ser  Phe
95                  100                      105                          110

GAC  GGA  AAT  GCC  CCC  GAT  GTG  AAG  GAC  AGA  GCC  GTT  TTG  ACA  GAT  TTC    745
Asp  Gly  Asn  Ala  Pro  Asp  Val  Lys  Asp  Arg  Ala  Val  Leu  Thr  Asp  Phe
                    115                      120                      125

GAA  TCG  ATT  CTT  ATT  GAA  TTC  CAC  AAA  TTG  AAA  CCA  GAA  TAT  CAA  GAA    793
Glu  Ser  Ile  Leu  Ile  Glu  Phe  His  Lys  Leu  Lys  Pro  Glu  Tyr  Gln  Glu
              130                      135                      140

GTC  ATC  AAG  GAG  ATC  ACC  GAG  AAA  ATG  GGT  AAT  GGT  ATG  GCC  GAC  TAC    841
Val  Ile  Lys  Glu  Ile  Thr  Glu  Lys  Met  Gly  Asn  Gly  Met  Ala  Asp  Tyr
         145                      150                      155
```

| | | | | | | | | | | | | | | | | |
|---|---|---|---|---|---|---|---|---|---|---|---|---|---|---|---|---|
| ATC | TTG | GAT | GAA | AAT | TAC | AAC | TTG | AAT | GGG | TTG | CAA | ACC | GTC | CAC | GAC | 889 |
| Ile | Leu | Asp | Glu | Asn | Tyr | Asn | Leu | Asn | Gly | Leu | Gln | Thr | Val | His | Asp | |
| | 160 | | | | 165 | | | | | 170 | | | | | | |
| TAC | GAC | GTG | TAC | TGT | CAC | TAC | GTA | GCT | GGT | TTG | GTC | GGT | GAT | GGT | TTG | 937 |
| Tyr | Asp | Val | Tyr | Cys | His | Tyr | Val | Ala | Gly | Leu | Val | Gly | Asp | Gly | Leu | |
| 175 | | | | | 180 | | | | | 185 | | | | | 190 | |
| ACC | CGT | TTG | ATT | GTC | ATT | GCC | AAG | TTT | GCC | AAC | GAA | TCT | TTG | TAT | TCT | 985 |
| Thr | Arg | Leu | Ile | Val | Ile | Ala | Lys | Phe | Ala | Asn | Glu | Ser | Leu | Tyr | Ser | |
| | | | | 195 | | | | | 200 | | | | | 205 | | |
| AAT | GAG | CAA | TTG | TAT | GAA | AGC | ATG | GGT | CTT | TTC | CTA | GAA | AAA | ACC | AAC | 1033 |
| Asn | Glu | Gln | Leu | Tyr | Glu | Ser | Met | Gly | Leu | Phe | Leu | Glu | Lys | Thr | Asn | |
| | | | 210 | | | | | 215 | | | | | 220 | | | |
| ATC | ATC | AGA | GAC | TAC | AAT | GAA | GAT | TTG | GTC | GAT | GGT | AGA | TCC | TTC | TGG | 1081 |
| Ile | Ile | Arg | Asp | Tyr | Asn | Glu | Asp | Leu | Val | Asp | Gly | Arg | Ser | Phe | Trp | |
| | | 225 | | | | | 230 | | | | | 235 | | | | |
| CCC | AAG | GAA | ATC | TGG | TCA | CAA | TAC | GCT | CCT | CAG | TTG | AAG | GAC | TTC | ATG | 1129 |
| Pro | Lys | Glu | Ile | Trp | Ser | Gln | Tyr | Ala | Pro | Gln | Leu | Lys | Asp | Phe | Met | |
| | 240 | | | | | 245 | | | | | 250 | | | | | |
| AAA | CCT | GAA | AAC | GAA | CAA | CTG | GGG | TTG | GAC | TGT | ATA | AAC | CAC | CTC | GTC | 1177 |
| Lys | Pro | Glu | Asn | Glu | Gln | Leu | Gly | Leu | Asp | Cys | Ile | Asn | His | Leu | Val | |
| 255 | | | | | 260 | | | | | 265 | | | | | 270 | |
| TTA | AAC | GCA | TTG | AGT | CAT | GTT | ATC | GAT | GTG | TTG | ACT | TAT | TTG | GCC | AGT | 1225 |
| Leu | Asn | Ala | Leu | Ser | His | Val | Ile | Asp | Val | Leu | Thr | Tyr | Leu | Ala | Ser | |
| | | | | 275 | | | | | 280 | | | | | 285 | | |
| ATC | CAC | GAG | CAA | TCC | ACT | TTC | CAA | TTT | TGT | GCC | ATT | CCC | CAA | GTT | ATG | 1273 |
| Ile | His | Glu | Gln | Ser | Thr | Phe | Gln | Phe | Cys | Ala | Ile | Pro | Gln | Val | Met | |
| | | | 290 | | | | | 295 | | | | | 300 | | | |
| GCC | ATT | GCA | ACC | TTG | GCT | TTG | GTA | TTC | AAC | AAC | CGT | GAA | GTG | CTA | CAT | 1321 |
| Ala | Ile | Ala | Thr | Leu | Ala | Leu | Val | Phe | Asn | Asn | Arg | Glu | Val | Leu | His | |
| | | 305 | | | | | 310 | | | | | 315 | | | | |
| GGC | AAT | GTA | AAG | ATT | CGT | AAG | GGT | ACT | ACC | TGC | TAT | TTA | ATT | TTG | AAA | 1369 |
| Gly | Asn | Val | Lys | Ile | Arg | Lys | Gly | Thr | Thr | Cys | Tyr | Leu | Ile | Leu | Lys | |
| | 320 | | | | | 325 | | | | | 330 | | | | | |
| TCA | AGG | ACT | TTG | CGT | GGC | TGT | GTC | GAG | ATT | TTT | GAC | TAT | TAC | TTA | CGT | 1417 |
| Ser | Arg | Thr | Leu | Arg | Gly | Cys | Val | Glu | Ile | Phe | Asp | Tyr | Tyr | Leu | Arg | |
| 335 | | | | | 340 | | | | | 345 | | | | | 350 | |
| GAT | ATC | AAA | TCT | AAA | TTG | GCT | GTG | CAA | GAT | CCA | AAT | TTC | TTA | AAA | TTG | 1465 |
| Asp | Ile | Lys | Ser | Lys | Leu | Ala | Val | Gln | Asp | Pro | Asn | Phe | Leu | Lys | Leu | |
| | | | | 355 | | | | | 360 | | | | | 365 | | |
| AAC | ATT | CAA | ATC | TCC | AAG | ATC | GAA | CAA | TTC | ATG | GAA | GAA | ATG | TAC | CAG | 1513 |
| Asn | Ile | Gln | Ile | Ser | Lys | Ile | Glu | Gln | Phe | Met | Glu | Glu | Met | Tyr | Gln | |
| | | | 370 | | | | | 375 | | | | | 380 | | | |
| GAT | AAA | TTA | CCT | CCT | AAC | GTG | AAG | CCA | AAT | GAA | ACT | CCA | ATT | TTC | TTG | 1561 |
| Asp | Lys | Leu | Pro | Pro | Asn | Val | Lys | Pro | Asn | Glu | Thr | Pro | Ile | Phe | Leu | |
| | | 385 | | | | | 390 | | | | | 395 | | | | |
| AAA | GTT | AAA | GAA | AGA | TCC | AGA | TAC | GAT | GAT | GAA | TTG | GTC | CCA | ACC | CAA | 1609 |
| Lys | Val | Lys | Glu | Arg | Ser | Arg | Tyr | Asp | Asp | Glu | Leu | Val | Pro | Thr | Gln | |
| | 400 | | | | | 405 | | | | | 410 | | | | | |
| CAA | GAA | GAA | GAG | TAC | AAG | TTC | AAT | ATG | GTT | TTA | TCT | ATC | ATC | TTG | TCC | 1657 |
| Gln | Glu | Glu | Glu | Tyr | Lys | Phe | Asn | Met | Val | Leu | Ser | Ile | Ile | Leu | Ser | |
| 415 | | | | | 420 | | | | | 425 | | | | | 430 | |
| GTT | CTT | CTT | GGG | TTT | TAT | TAT | ATA | TAC | ACT | TTA | CAC | AGA | GCG | | | 1699 |
| Val | Leu | Leu | Gly | Phe | Tyr | Tyr | Ile | Tyr | Thr | Leu | His | Arg | Ala | | | |
| | | | | 435 | | | | | 440 | | | | | | | |

```
TGAAGTCTGC GCCAAATAAC ATAAACAAAC AACTCCGAAC AATAACTAAG TACTTACATA    1759

ATAGGTAGAG GCCTATCCTT AAAGATAACC TTATATTTCA TTACATCAAC TAATTCGACC    1819

TTATTATCTT TCGAATTGAA ATGCATTATA CCCATCGGTA CGTCTAGCTT TGTCACCTTC    1879

CCCAGTAAAC GTTGTTTCTT GCCGACAAAC AATGTGGCCC TCTCTCCGTC AATCTGTAAC    1939
```

```
GACCCAAATC GTATTAAAGT TTCGCCGTCC TGTTCACTGA ACCTTCCCTC ATTTGGAGAA    1999

TCTCTCCTCG CCAGCGACGC AAAGTCCTTA GGCAACTCTA GTTCACCTTG AATCT         2054
```

( 2 ) INFORMATION FOR SEQ ID NO:2:

( i ) SEQUENCE CHARACTERISTICS:
    ( A ) LENGTH: 444 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Met Gly Lys Leu Leu Gln Leu Ala Leu His Pro Val Glu Met Lys Ala
 1               5                  10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
                100                 105                 110

Asn Ala Pro Asp Val Lys Asp Arg Ala Val Leu Thr Asp Phe Glu Ser
            115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
                180                 185                 190

Leu Ile Val Ile Ala Lys Phe Ala Asn Glu Ser Leu Tyr Ser Asn Glu
            195                 200                 205

Gln Leu Tyr Glu Ser Met Gly Leu Phe Leu Glu Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
                260                 265                 270

Ala Leu Ser His Val Ile Asp Val Leu Thr Tyr Leu Ala Ser Ile His
            275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
```

|   |   |   |   |   |   | 340 |   |   |   |   | 345 |   |   |   |   | 350 |   |
|---|---|---|---|---|---|---|---|---|---|---|---|---|---|---|---|---|---|
| Lys | Ser | Lys | Leu | Ala | Val | Gln | Asp | Pro | Asn | Phe | Leu | Lys | Leu | Asn | Ile |
|   |   | 355 |   |   |   | 360 |   |   |   | 365 |   |   |   |   |   |
| Gln | Ile | Ser | Lys | Ile | Glu | Gln | Phe | Met | Glu | Glu | Met | Tyr | Gln | Asp | Lys |
|   |   | 370 |   |   |   | 375 |   |   |   | 380 |   |   |   |   |   |
| Leu | Pro | Pro | Asn | Val | Lys | Pro | Asn | Glu | Thr | Pro | Ile | Phe | Leu | Lys | Val |
| 385 |   |   |   | 390 |   |   |   | 395 |   |   |   |   |   | 400 |   |
| Lys | Glu | Arg | Ser | Arg | Tyr | Asp | Asp | Glu | Leu | Val | Pro | Thr | Gln | Gln | Glu |
|   |   |   | 405 |   |   |   | 410 |   |   |   |   | 415 |   |   |   |
| Glu | Glu | Tyr | Lys | Phe | Asn | Met | Val | Leu | Ser | Ile | Ile | Leu | Ser | Val | Leu |
|   |   |   | 420 |   |   |   | 425 |   |   |   | 430 |   |   |   |   |
| Leu | Gly | Phe | Tyr | Tyr | Ile | Tyr | Thr | Leu | His | Arg | Ala |
|   |   | 435 |   |   |   | 440 |   |   |   |   |   |

( 2 ) INFORMATION FOR SEQ ID NO:3:

( i ) SEQUENCE CHARACTERISTICS:
        ( A ) LENGTH: 1479 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 19..1398

( x i ) SEQUENCE DESCRIPTION: SEQ ID NO:3:

| CTAAAGGCGT | TTTATATA | ATG<br>Met<br>1 | AGT<br>Ser | TTA<br>Leu | GCT<br>Ala | AAC<br>Asn<br>5 | CGC<br>Arg | ATT<br>Ile | GAA<br>Glu | GAA<br>Glu | ATC<br>Ile<br>10 | CGG<br>Arg | 51 |
|---|---|---|---|---|---|---|---|---|---|---|---|---|---|
| TGC<br>Cys | CTT<br>Leu | TGT<br>Cys<br>15 | CAG<br>Gln | TAC<br>Tyr | AAG<br>Lys | CTT<br>Leu | TGG<br>Trp<br>20 | AAT<br>Asn | GAC<br>Asp | CTT<br>Leu | CCT<br>Pro | TCT<br>Ser<br>25 | TAT<br>Tyr | GGA<br>Gly | GAA<br>Glu | 99 |
| GAC<br>Asp | GAA<br>Glu | AAT<br>Asn<br>30 | GTG<br>Val | CCT<br>Pro | CAA<br>Gln | AAC<br>Asn | ATC<br>Ile<br>35 | CGC<br>Arg | CGT<br>Arg | TGT<br>Cys | TAC<br>Tyr | CAA<br>Gln<br>40 | TTA<br>Leu | CTC<br>Leu | GAT<br>Asp | 147 |
| ATG<br>Met | ACC<br>Thr | TCG<br>Ser<br>45 | AGA<br>Arg | TCC<br>Ser | TTT<br>Phe | GCA<br>Ala<br>50 | GTC<br>Val | GTT<br>Val | ATT<br>Ile | AAA<br>Lys | GAA<br>Glu<br>55 | TTG<br>Leu | CCA<br>Pro | AAT<br>Asn | GGT<br>Gly | 195 |
| ATT<br>Ile<br>60 | AGA<br>Arg | GAG<br>Glu | GCT<br>Ala | GTT<br>Val | ATG<br>Met<br>65 | ATT<br>Ile | TTT<br>Phe | TAT<br>Tyr | CTT<br>Leu | GTC<br>Val<br>70 | CTT<br>Leu | CGT<br>Arg | GGA<br>Gly | CTG<br>Leu | GAT<br>Asp<br>75 | 243 |
| ACA<br>Thr | GTA<br>Val | GAG<br>Glu | GAT<br>Asp | GAC<br>Asp<br>80 | ATG<br>Met | ACG<br>Thr | TTG<br>Leu | CCT<br>Pro | TTG<br>Leu<br>85 | GAT<br>Asp | AAA<br>Lys | AAG<br>Lys | CTT<br>Leu | CCA<br>Pro<br>90 | ATC<br>Ile | 291 |
| CTA<br>Leu | AGA<br>Arg | GAT<br>Asp | TTT<br>Phe<br>95 | TAT<br>Tyr | AAA<br>Lys | ACA<br>Thr | ATT<br>Ile | GAA<br>Glu<br>100 | GTC<br>Val | GAA<br>Glu | GGG<br>Gly | TGG<br>Trp | ACG<br>Thr<br>105 | TTT<br>Phe | AAT<br>Asn | 339 |
| GAA<br>Glu | TCT<br>Ser | GGT<br>Gly<br>110 | CCT<br>Pro | AAC<br>Asn | GAA<br>Glu | AAG<br>Lys | GAT<br>Asp<br>115 | CGT<br>Arg | CAG<br>Gln | CTT<br>Leu | CTC<br>Leu | GTA<br>Val<br>120 | GAA<br>Glu | TTC<br>Phe | GAC<br>Asp | 387 |
| GTG<br>Val | GTT<br>Val | ATA<br>Ile<br>125 | AAA<br>Lys | GAA<br>Glu | TAT<br>Tyr | CTT<br>Leu | AAC<br>Asn<br>130 | CTG<br>Leu | TCA<br>Ser | GAG<br>Glu | GGT<br>Gly | TAT<br>Tyr<br>135 | CGT<br>Arg | AAT<br>Asn | GTT<br>Val | 435 |
| ATT<br>Ile | TCG<br>Ser | AAC<br>Asn<br>140 | ATT<br>Ile | ACT<br>Thr | AAG<br>Lys | GAA<br>Glu<br>145 | ATG<br>Met | GGT<br>Gly | GAT<br>Asp | GGT<br>Gly | ATG<br>Met<br>150 | GCT<br>Ala | TAT<br>Tyr | TAT<br>Tyr | GCC<br>Ala<br>155 | 483 |
| TCT<br>Ser | CTT<br>Leu | GCC<br>Ala | GAA<br>Glu | AAA<br>Lys<br>160 | AAT<br>Asn | GAC<br>Asp | GGA<br>Gly | TTC<br>Phe | TCT<br>Ser<br>165 | GTA<br>Val | GAA<br>Glu | ACT<br>Thr | ATA<br>Ile | GAA<br>Glu<br>170 | GAC<br>Asp | 531 |

|  |  |  |  |  |  |  |  |  |  |  |  |  |  |  |  |
|---|---|---|---|---|---|---|---|---|---|---|---|---|---|---|---|
| TTT | AAC | AAA | TAT | TGT | CAT | TAT | GTT | GCC | GGA | TTG | GTG | GGA | ATT | GGA | CTA |
| Phe | Asn | Lys | Tyr | Cys | His | Tyr | Val | Ala | Gly | Leu | Val | Gly | Ile | Gly | Leu |
|  |  | 175 |  |  |  |  | 180 |  |  |  |  | 185 |  |  |  | 579

|  |  |  |  |  |  |  |  |  |  |  |  |  |  |  |  |
|---|---|---|---|---|---|---|---|---|---|---|---|---|---|---|---|
| TCT | CGT | TTG | TTT | GCT | CAA | TCT | AAG | CTA | GAA | GAT | CCG | GAT | TTA | GCT | CAT |
| Ser | Arg | Leu | Phe | Ala | Gln | Ser | Lys | Leu | Glu | Asp | Pro | Asp | Leu | Ala | His |
|  |  | 190 |  |  |  |  | 195 |  |  |  |  | 200 |  |  |  | 627

AGT CAA GCT ATT TCC AAT TCT CTT GGA CTC TTT TTA CAA AAA GTT AAC  675
Ser Gln Ala Ile Ser Asn Ser Leu Gly Leu Phe Leu Gln Lys Val Asn
    205             210             215

ATC ATT CGT GAT TAT CGT GAG GAT TTT GAT GAT AAT CGT CAT TTC TGG  723
Ile Ile Arg Asp Tyr Arg Glu Asp Phe Asp Asp Asn Arg His Phe Trp
220             225             230             235

CCT CGT GAA ATT TGG TCC AAG TAT ACT TCC AGT TTC GGT GAT CTC TGT  771
Pro Arg Glu Ile Trp Ser Lys Tyr Thr Ser Ser Phe Gly Asp Leu Cys
            240             245             250

CTT CCT GAC AAC TCT GAA AAA GCT CTT GAA TGT TTA TCT GAT ATG ACT  819
Leu Pro Asp Asn Ser Glu Lys Ala Leu Glu Cys Leu Ser Asp Met Thr
            255             260             265

GCT AAT GCT TTA ACA CAT GCT ACT GAT GCT CTC GTT TAT CTT TCT CAA  867
Ala Asn Ala Leu Thr His Ala Thr Asp Ala Leu Val Tyr Leu Ser Gln
        270             275             280

TTG AAG ACT CAG GAA ATA TTT AAT TTC TGT GCT ATT CCA CAA GTA ATG  915
Leu Lys Thr Gln Glu Ile Phe Asn Phe Cys Ala Ile Pro Gln Val Met
    285             290             295

GCA ATT GCC ACA TTA GCT GCA GTT TTC AGA AAC CCG GAT GTT TTT CAA  963
Ala Ile Ala Thr Leu Ala Ala Val Phe Arg Asn Pro Asp Val Phe Gln
300             305             310             315

ACT AAT GTT AAG ATA AGG AAG GGT CAG GCT GTC CAG ATT ATT CTA CAT  1011
Thr Asn Val Lys Ile Arg Lys Gly Gln Ala Val Gln Ile Ile Leu His
            320             325             330

TCT GTA AAC TTG AAG AAT GTT TGT GAT TTA TTC CTT CGT TAC ACC CGT  1059
Ser Val Asn Leu Lys Asn Val Cys Asp Leu Phe Leu Arg Tyr Thr Arg
        335             340             345

GAT ATT CAT TAT AAG AAC ACT CCT AAA GAT CCC AAC TTT TTG AAG ATT  1107
Asp Ile His Tyr Lys Asn Thr Pro Lys Asp Pro Asn Phe Leu Lys Ile
        350             355             360

TCA ATT GAA TGT GGA AAG ATT GAG CAA GTA TCT GAA AGC TTA TTT CCA  1155
Ser Ile Glu Cys Gly Lys Ile Glu Gln Val Ser Glu Ser Leu Phe Pro
365             370             375

CGG CGC TTC CGT GAG ATG TAC GAA AAG GCC TAT GTT AGT AAG TTG TCT  1203
Arg Arg Phe Arg Glu Met Tyr Glu Lys Ala Tyr Val Ser Lys Leu Ser
380             385             390             395

GAA CAA AAG AAG GGA AAC GGA ACT CAG AAG GCA ATT TTA AAT GAC GAG  1251
Glu Gln Lys Lys Gly Asn Gly Thr Gln Lys Ala Ile Leu Asn Asp Glu
            400             405             410

CAA AAG GAA TTG TAT CGA AAG GAT TTA CAG AAA CTA GGC ATT AGC ATT  1299
Gln Lys Glu Leu Tyr Arg Lys Asp Leu Gln Lys Leu Gly Ile Ser Ile
        415             420             425

CTT TTT GTA TTT TTT ATA ATC CTT GTA TGC CTT GCT GTC ATT TTC TAT  1347
Leu Phe Val Phe Phe Ile Ile Leu Val Cys Leu Ala Val Ile Phe Tyr
        430             435             440

GTG TTC AAT ATT AGA ATA CAT TGG TCA GAC TTC AAA GAG CTT AAT TTG  1395
Val Phe Asn Ile Arg Ile His Trp Ser Asp Phe Lys Glu Leu Asn Leu
    445             450             455

TTT TAGTCCGTAA ATTTAAAAAA CTTAAATACT GGTTCAATAT CGATAATATA  1448
Phe
460

CAAGCAGTTT AAAAAAAAAA AAAAAAACTT T  1479

( 2 ) INFORMATION FOR SEQ ID NO:4:

( i ) SEQUENCE CHARACTERISTICS:
        ( A ) LENGTH: 460 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Leu Ala Asn Arg Ile Glu Glu Ile Arg Cys Leu Cys Gln Tyr
  1               5                  10                  15

Lys Leu Trp Asn Asp Leu Pro Ser Tyr Gly Glu Asp Glu Asn Val Pro
             20                  25                  30

Gln Asn Ile Arg Arg Cys Tyr Gln Leu Leu Asp Met Thr Ser Arg Ser
             35                  40                  45

Phe Ala Val Val Ile Lys Glu Leu Pro Asn Gly Ile Arg Glu Ala Val
     50                  55                  60

Met Ile Phe Tyr Leu Val Leu Arg Gly Leu Asp Thr Val Glu Asp Asp
 65                  70                  75                  80

Met Thr Leu Pro Leu Asp Lys Lys Leu Pro Ile Leu Arg Asp Phe Tyr
                 85                  90                  95

Lys Thr Ile Glu Val Glu Gly Trp Thr Phe Asn Glu Ser Gly Pro Asn
            100                 105                 110

Glu Lys Asp Arg Gln Leu Leu Val Glu Phe Asp Val Val Ile Lys Glu
            115                 120                 125

Tyr Leu Asn Leu Ser Glu Gly Tyr Arg Asn Val Ile Ser Asn Ile Thr
        130                 135                 140

Lys Glu Met Gly Asp Gly Met Ala Tyr Tyr Ala Ser Leu Ala Glu Lys
145                 150                 155                 160

Asn Asp Gly Phe Ser Val Glu Thr Ile Glu Asp Phe Asn Lys Tyr Cys
                165                 170                 175

His Tyr Val Ala Gly Leu Val Gly Ile Gly Leu Ser Arg Leu Phe Ala
            180                 185                 190

Gln Ser Lys Leu Glu Asp Pro Asp Leu Ala His Ser Gln Ala Ile Ser
        195                 200                 205

Asn Ser Leu Gly Leu Phe Leu Gln Lys Val Asn Ile Ile Arg Asp Tyr
    210                 215                 220

Arg Glu Asp Phe Asp Asp Asn Arg His Phe Trp Pro Arg Glu Ile Trp
225                 230                 235                 240

Ser Lys Tyr Thr Ser Ser Phe Gly Asp Leu Cys Leu Pro Asp Asn Ser
                245                 250                 255

Glu Lys Ala Leu Glu Cys Leu Ser Asp Met Thr Ala Asn Ala Leu Thr
            260                 265                 270

His Ala Thr Asp Ala Leu Val Tyr Leu Ser Gln Leu Lys Thr Gln Glu
        275                 280                 285

Ile Phe Asn Phe Cys Ala Ile Pro Gln Val Met Ala Ile Ala Thr Leu
    290                 295                 300

Ala Ala Val Phe Arg Asn Pro Asp Val Phe Gln Thr Asn Val Lys Ile
305                 310                 315                 320

Arg Lys Gly Gln Ala Val Gln Ile Ile Leu His Ser Val Asn Leu Lys
                325                 330                 335

Asn Val Cys Asp Leu Phe Leu Arg Tyr Thr Arg Asp Ile His Tyr Lys
            340                 345                 350

Asn Thr Pro Lys Asp Pro Asn Phe Leu Lys Ile Ser Ile Glu Cys Gly
        355                 360                 365
```

| | | | | | | | | | | | | | | |
|---|---|---|---|---|---|---|---|---|---|---|---|---|---|---|
| Lys | Ile | Glu | Gln | Val | Ser | Glu | Ser | Leu | Phe | Pro | Arg | Arg | Phe | Arg | Glu |
| | 370 | | | | 375 | | | | | 380 | | | | | |
| Met | Tyr | Glu | Lys | Ala | Tyr | Val | Ser | Lys | Leu | Ser | Glu | Gln | Lys | Lys | Gly |
| 385 | | | | | 390 | | | | | 395 | | | | | 400 |
| Asn | Gly | Thr | Gln | Lys | Ala | Ile | Leu | Asn | Asp | Glu | Gln | Lys | Glu | Leu | Tyr |
| | | | | 405 | | | | | 410 | | | | | 415 | |
| Arg | Lys | Asp | Leu | Gln | Lys | Leu | Gly | Ile | Ser | Ile | Leu | Phe | Val | Phe | Phe |
| | | | 420 | | | | | 425 | | | | | 430 | | |
| Ile | Ile | Leu | Val | Cys | Leu | Ala | Val | Ile | Phe | Tyr | Val | Phe | Asn | Ile | Arg |
| | | 435 | | | | | 440 | | | | | 445 | | | |
| Ile | His | Trp | Ser | Asp | Phe | Lys | Glu | Leu | Asn | Leu | Phe | | | | |
| | 450 | | | | | 455 | | | | | 460 | | | | |

( 2 ) INFORMATION FOR SEQ ID NO:5:

( i ) SEQUENCE CHARACTERISTICS:
    ( A ) LENGTH: 1349 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: 10..1260

( x i ) SEQUENCE DESCRIPTION: SEQ ID NO:5:

| | | | | | | | | | | | | | | |
|---|---|---|---|---|---|---|---|---|---|---|---|---|---|---|
| TGCGCCAGG | ATG | GAG | TTC | GTG | AAA | TGC | CTT | GGC | CAC | CCC | GAA | GAG | TTC | 48 |
| | Met | Glu | Phe | Val | Lys | Cys | Leu | Gly | His | Pro | Glu | Glu | Phe | |
| | 1 | | | | 5 | | | | | 10 | | | | |
| TAC | AAC | CTG | GTG | CGC | TTC | CGG | ATC | GGG | GGC | AAG | CGG | AAG | GTG | ATG | CCC | 96 |
| Tyr | Asn | Leu | Val | Arg | Phe | Arg | Ile | Gly | Gly | Lys | Arg | Lys | Val | Met | Pro |
| | 15 | | | | | 20 | | | | | 25 | | | | |
| AAG | ATG | GAC | CAG | GAC | TCG | CTC | AGC | AGC | AGC | CTG | AAA | ACT | TGC | TAC | AAG | 144 |
| Lys | Met | Asp | Gln | Asp | Ser | Leu | Ser | Ser | Ser | Leu | Lys | Thr | Cys | Tyr | Lys |
| 30 | | | | | 35 | | | | | 40 | | | | | 45 |
| TAT | CTC | AAT | CAG | ACC | AGT | CGC | AGT | TTC | GCA | GCT | GTT | ATC | CAG | GCG | CTG | 192 |
| Tyr | Leu | Asn | Gln | Thr | Ser | Arg | Ser | Phe | Ala | Ala | Val | Ile | Gln | Ala | Leu |
| | | | | 50 | | | | | 55 | | | | | 60 | |
| GAT | GGG | GAA | ATG | CGC | AAC | GCA | GTG | TGC | ATA | TTT | TAT | CTG | GTT | CTC | CGA | 240 |
| Asp | Gly | Glu | Met | Arg | Asn | Ala | Val | Cys | Ile | Phe | Tyr | Leu | Val | Leu | Arg |
| | | | 65 | | | | | 70 | | | | | 75 | | |
| GCT | CTG | GAC | ACA | CTG | GAA | GAT | GAC | ATG | ACC | ATC | AGT | GTG | GAA | AAG | AAG | 288 |
| Ala | Leu | Asp | Thr | Leu | Glu | Asp | Asp | Met | Thr | Ile | Ser | Val | Glu | Lys | Lys |
| | | | 80 | | | | | 85 | | | | | 90 | | |
| GTC | CCG | CTG | TTA | CAC | AAC | TTT | CAC | TCT | TTC | CTT | TAC | CAA | CCA | GAC | TGG | 336 |
| Val | Pro | Leu | Leu | His | Asn | Phe | His | Ser | Phe | Leu | Tyr | Gln | Pro | Asp | Trp |
| | 95 | | | | | 100 | | | | | 105 | | | | |
| CGG | TTC | ATG | GAG | AGC | AAG | GAG | AAG | GAT | CGC | CAG | GTG | CTG | GAG | GAC | TTC | 384 |
| Arg | Phe | Met | Glu | Ser | Lys | Glu | Lys | Asp | Arg | Gln | Val | Leu | Glu | Asp | Phe |
| 110 | | | | | 115 | | | | | 120 | | | | | 125 |
| CCA | ACG | ATC | TCC | CTT | GAG | TTT | AGA | AAT | CTG | GCT | GAG | AAA | TAC | CAA | ACA | 432 |
| Pro | Thr | Ile | Ser | Leu | Glu | Phe | Arg | Asn | Leu | Ala | Glu | Lys | Tyr | Gln | Thr |
| | | | | 130 | | | | | 135 | | | | | 140 | |
| GTG | ATT | GCC | GAC | ATT | TGC | CGG | AGA | ATG | GGC | ATT | GGG | ATG | GCA | GAG | TTT | 480 |
| Val | Ile | Ala | Asp | Ile | Cys | Arg | Arg | Met | Gly | Ile | Gly | Met | Ala | Glu | Phe |
| | | | 145 | | | | | 150 | | | | | 155 | | |
| TTG | GAT | AAG | CAT | GTG | ACC | TCT | GAA | CAG | GAG | TGG | GAC | AAG | TAC | TGC | CAC | 528 |
| Leu | Asp | Lys | His | Val | Thr | Ser | Glu | Gln | Glu | Trp | Asp | Lys | Tyr | Cys | His |
| | | 160 | | | | | 165 | | | | | 170 | | | |
| TAT | GTT | GCT | GGG | CTG | GTC | GGA | ATT | GGC | CTT | TCC | CGT | CTT | TTC | TCA | GCC | 576 |

| | | | | | | | | | | | | | | |
|---|---|---|---|---|---|---|---|---|---|---|---|---|---|---|
|Tyr|Val|Ala|Gly|Leu|Val|Gly|Ile|Gly|Leu|Ser|Arg|Leu|Phe|Ser|Ala|
| |175| | | |180| | | | |185| | | | |

```
TCA  GAG  TTT  GAA  GAC  CCC  TTA  GTT  GGT  GAA  GAT  ACA  GAA  CGT  GCC  AAC      624
Ser  Glu  Phe  Glu  Asp  Pro  Leu  Val  Gly  Glu  Asp  Thr  Glu  Arg  Ala  Asn
190            Phe       195                           200                      205

TCT  ATG  GGC  CTG  TTT  CTG  CAG  AAA  ACA  AAC  ATC  ATC  CGT  GAC  TAT  CTG      672
Ser  Met  Gly  Leu  Phe  Leu  Gln  Lys  Thr  Asn  Ile  Ile  Arg  Asp  Tyr  Leu
                         210                      215                      220

GAA  GAC  CAG  CAA  GGA  GGA  AGA  GAG  TTC  TGG  CCT  CAA  GAG  GTT  TGG  AGC      720
Glu  Asp  Gln  Gln  Gly  Gly  Arg  Glu  Phe  Trp  Pro  Gln  Glu  Val  Trp  Ser
                    225                      230                      235

AGG  TAT  GTT  AAG  AAG  TTA  GGG  GAT  TTT  GCT  AAG  CCG  GAG  AAT  ATT  GAC      768
Arg  Tyr  Val  Lys  Lys  Leu  Gly  Asp  Phe  Ala  Lys  Pro  Glu  Asn  Ile  Asp
          240                      245                      250

TTG  GCC  GTG  CAG  TGC  CTG  AAT  GAA  CTT  ATA  ACC  AAT  GCA  CTG  CAC  CAC      816
Leu  Ala  Val  Gln  Cys  Leu  Asn  Glu  Leu  Ile  Thr  Asn  Ala  Leu  His  His
     255                      260                      265

ATC  CCA  GAT  GTC  ATC  ACC  TAC  CTT  TCG  AGA  CTC  AGA  AAC  CAG  AGT  GTG      864
Ile  Pro  Asp  Val  Ile  Thr  Tyr  Leu  Ser  Arg  Leu  Arg  Asn  Gln  Ser  Val
270                 275                      280                      285

TTT  AAC  TTC  TGC  GCT  ATT  CCA  CAG  GTG  ATG  GCC  ATT  GCC  ACT  TTG  GCT      912
Phe  Asn  Phe  Cys  Ala  Ile  Pro  Gln  Val  Met  Ala  Ile  Ala  Thr  Leu  Ala
                    290                      295                      300

GCC  TGT  TAT  AAT  AAC  CAG  CAG  GTG  TTC  AAA  GGG  GCA  GTG  AAG  ATT  CGG      960
Ala  Cys  Tyr  Asn  Asn  Gln  Gln  Val  Phe  Lys  Gly  Ala  Val  Lys  Ile  Arg
               305                      310                      315

AAA  GGG  CAA  GCA  GTG  ACC  CTG  ATG  ATG  GAT  GCC  ACC  AAT  ATG  CCA  GCT     1008
Lys  Gly  Gln  Ala  Val  Thr  Leu  Met  Met  Asp  Ala  Thr  Asn  Met  Pro  Ala
          320                      325                      330

GTC  AAA  GCC  ATC  ATA  TAT  CAG  TAT  ATG  GAA  GAG  ATT  TAT  CAT  AGA  ATC     1056
Val  Lys  Ala  Ile  Ile  Tyr  Gln  Tyr  Met  Glu  Glu  Ile  Tyr  His  Arg  Ile
     335                      340                      345

CCC  GAC  TCA  GAC  CCA  TCT  TCT  AGC  AAA  ACA  AGG  CAG  ATC  ATC  TCC  ACC     1104
Pro  Asp  Ser  Asp  Pro  Ser  Ser  Ser  Lys  Thr  Arg  Gln  Ile  Ile  Ser  Thr
350                 355                      360                      365

ATC  CGG  ACG  CAG  AAT  CTT  CCC  AAC  TGT  CAG  CTG  ATT  TCC  CGA  AGC  CAC     1152
Ile  Arg  Thr  Gln  Asn  Leu  Pro  Asn  Cys  Gln  Leu  Ile  Ser  Arg  Ser  His
               370                      375                      380

TAC  TCC  CCC  ATC  TAC  CTG  TCG  TTT  GTC  ATG  CTT  TTG  GCT  GCC  CTG  AGC     1200
Tyr  Ser  Pro  Ile  Tyr  Leu  Ser  Phe  Val  Met  Leu  Leu  Ala  Ala  Leu  Ser
               385                      390                      395

TGG  CAG  TAC  CTG  ACC  ACT  CTC  TCC  CAG  GTA  ACA  GAA  GAC  TAT  GTT  CAG     1248
Trp  Gln  Tyr  Leu  Thr  Thr  Leu  Ser  Gln  Val  Thr  Glu  Asp  Tyr  Val  Gln
          400                      405                      410

ACT  GGA  GAA  CAC  TGATCCCAAA  TTTGTCCATA  GCTGAAGTCC  ACCATAAAGT              1300
Thr  Gly  Glu  His
               415

GGATTTACTT  TTTTTCTTTA  AAAAAAAAAA  AAAAAAAAAA  AAAAAAAA                        1349
```

( 2 ) INFORMATION FOR SEQ ID NO:6:

( i ) SEQUENCE CHARACTERISTICS:
        ( A ) LENGTH: 417 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Glu  Phe  Val  Lys  Cys  Leu  Gly  His  Pro  Glu  Glu  Phe  Tyr  Asn  Leu
1              5                        10                       15
```

-continued

| | | | | | | | | | | | | | |
|---|---|---|---|---|---|---|---|---|---|---|---|---|---|
| Val | Arg | Phe | Arg 20 | Ile | Gly | Gly | Lys | Arg 25 | Val | Met | Pro | Lys 30 | Met | Asp |
| Gln | Asp | Ser 35 | Leu | Ser | Ser | Ser | Leu 40 | Lys | Thr | Cys | Tyr | Lys 45 | Tyr | Leu | Asn |
| Gln | Thr 50 | Ser | Arg | Ser | Phe | Ala 55 | Ala | Val | Ile | Gln | Ala 60 | Leu | Asp | Gly | Glu |
| Met 65 | Arg | Asn | Ala | Val | Cys 70 | Ile | Phe | Tyr | Leu | Val 75 | Leu | Arg | Ala | Leu | Asp 80 |
| Thr | Leu | Glu | Asp | Asp 85 | Met | Thr | Ile | Ser | Val 90 | Glu | Lys | Lys | Val | Pro 95 | Leu |
| Leu | His | Asn | Phe 100 | His | Ser | Phe | Leu | Tyr 105 | Gln | Pro | Asp | Trp | Arg 110 | Phe | Met |
| Glu | Ser | Lys 115 | Glu | Lys | Asp | Arg | Gln 120 | Val | Leu | Glu | Asp | Phe 125 | Pro | Thr | Ile |
| Ser | Leu 130 | Glu | Phe | Arg | Asn | Leu 135 | Ala | Glu | Lys | Tyr | Gln 140 | Thr | Val | Ile | Ala |
| Asp 145 | Ile | Cys | Arg | Arg | Met 150 | Gly | Ile | Gly | Met | Ala 155 | Glu | Phe | Leu | Asp | Lys 160 |
| His | Val | Thr | Ser | Glu 165 | Gln | Glu | Trp | Asp | Lys 170 | Tyr | Cys | His | Tyr | Val 175 | Ala |
| Gly | Leu | Val | Gly 180 | Ile | Gly | Leu | Ser | Arg 185 | Leu | Phe | Ser | Ala | Ser 190 | Glu | Phe |
| Glu | Asp | Pro 195 | Leu | Val | Gly | Glu | Asp 200 | Thr | Glu | Arg | Ala | Asn 205 | Ser | Met | Gly |
| Leu | Phe 210 | Leu | Gln | Lys | Thr | Asn 215 | Ile | Ile | Arg | Asp | Tyr 220 | Leu | Glu | Asp | Gln |
| Gln 225 | Gly | Gly | Arg | Glu | Phe 230 | Trp | Pro | Gln | Glu | Val 235 | Trp | Ser | Arg | Tyr | Val 240 |
| Lys | Lys | Leu | Gly | Asp 245 | Phe | Ala | Lys | Pro | Glu 250 | Asn | Ile | Asp | Leu | Ala 255 | Val |
| Gln | Cys | Leu | Asn 260 | Glu | Leu | Ile | Thr | Asn 265 | Ala | Leu | His | His | Ile 270 | Pro | Asp |
| Val | Ile | Thr 275 | Tyr | Leu | Ser | Arg | Leu 280 | Arg | Asn | Gln | Ser | Val 285 | Phe | Asn | Phe |
| Cys | Ala 290 | Ile | Pro | Gln | Val | Met 295 | Ala | Ile | Ala | Thr | Leu 300 | Ala | Ala | Cys | Tyr |
| Asn 305 | Asn | Gln | Gln | Val | Phe 310 | Lys | Gly | Ala | Val | Lys 315 | Ile | Arg | Lys | Gly | Gln 320 |
| Ala | Val | Thr | Leu | Met 325 | Met | Asp | Ala | Thr | Asn 330 | Met | Pro | Ala | Val | Lys 335 | Ala |
| Ile | Ile | Tyr | Gln 340 | Tyr | Met | Glu | Glu | Ile 345 | Tyr | His | Arg | Ile | Pro 350 | Asp | Ser |
| Asp | Pro | Ser 355 | Ser | Ser | Lys | Thr | Arg 360 | Gln | Ile | Ile | Ser | Thr 365 | Ile | Arg | Thr |
| Gln | Asn 370 | Leu | Pro | Asn | Cys | Gln 375 | Leu | Ile | Ser | Arg | Ser 380 | His | Tyr | Ser | Pro |
| Ile 385 | Tyr | Leu | Ser | Phe | Val 390 | Met | Leu | Leu | Ala | Ala 395 | Leu | Ser | Trp | Gln | Tyr 400 |
| Leu | Thr | Thr | Leu | Ser 405 | Gln | Val | Thr | Glu | Asp 410 | Tyr | Val | Gln | Thr | Gly 415 | Glu |
| His | | | | | | | | | | | | | | | |

(2) INFORMATION FOR SEQ ID NO:7:

(i) SEQUENCE CHARACTERISTICS:
  (A) LENGTH: 417 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO:7:

```
Met Glu Phe Val Lys Cys Leu Gly His Pro Glu Glu Phe Tyr Asn Leu
 1               5                  10                  15

Val Arg Phe Arg Ile Gly Gly Lys Arg Lys Val Met Pro Lys Met Asp
                20                  25                  30

Gln Asp Ser Leu Ser Ser Ser Leu Lys Thr Cys Tyr Lys Tyr Leu Asn
                35                  40                  45

Gln Thr Ser Arg Ser Phe Ala Ala Val Ile Gln Ala Leu Asp Gly Glu
        50                  55                  60

Met Arg Asn Ala Val Cys Ile Phe Tyr Leu Val Leu Arg Ala Leu Asp
 65                  70                  75                  80

Thr Leu Glu Asp Asp Met Thr Ile Ser Val Glu Lys Lys Val Pro Leu
                    85                  90                  95

Leu His Asn Phe His Ser Phe Leu Tyr Gln Pro Asp Trp Arg Phe Met
                100                 105                 110

Glu Ser Lys Glu Lys Asp Arg Gln Val Leu Glu Asp Phe Pro Thr Ile
            115                 120                 125

Ser Leu Glu Phe Arg Asn Leu Ala Glu Lys Tyr Gln Thr Val Ile Ala
    130                 135                 140

Asp Ile Cys Arg Arg Met Gly Ile Gly Met Ala Glu Phe Leu Asp Lys
145                 150                 155                 160

His Val Thr Ser Glu Gln Glu Trp Asp Lys Tyr Cys His Tyr Val Ala
                165                 170                 175

Gly Leu Val Gly Ile Gly Leu Ser Arg Leu Phe Ser Ala Ser Glu Phe
                180                 185                 190

Glu Asp Pro Leu Val Gly Glu Asp Thr Glu Arg Ala Asn Ser Met Gly
            195                 200                 205

Leu Phe Leu Gln Lys Ile Asn Ile Ile Arg Asp Tyr Leu Glu Asp Gln
    210                 215                 220

Gln Gly Gly Arg Glu Phe Trp Pro Gln Glu Val Trp Ser Arg Tyr Val
225                 230                 235                 240

Lys Lys Leu Gly Asp Phe Ala Lys Pro Glu Asn Ile Asp Leu Ala Val
                245                 250                 255

Gln Cys Leu Asn Glu Leu Ile Thr Asn Ala Leu His His Ile Pro Asp
                260                 265                 270

Val Ile Thr Tyr Leu Ser Arg Leu Arg Asn Gln Ser Val Phe Asn Phe
            275                 280                 285

Cys Ala Ile Pro Gln Val Met Ala Ile Ala Thr Leu Ala Ala Cys Tyr
    290                 295                 300

Asn Asn Gln Gln Val Phe Lys Gly Ala Val Lys Ile Arg Lys Gly Gln
305                 310                 315                 320

Ala Val Thr Leu Met Met Asp Ala Thr Asn Met Pro Ala Val Lys Ala
                325                 330                 335

Ile Ile Tyr Gln Tyr Met Glu Glu Ile Tyr His Arg Ile Pro Asp Ser
                340                 345                 350

Asp Pro Ser Ser Ser Lys Thr Arg Gln Ile Ile Ser Thr Ile Arg Thr
            355                 360                 365

Gln Asn Leu Pro Asn Cys Gln Leu Ile Ser Arg Ser His Tyr Ser Pro
```

```
              370                     375                     380
Ile  Tyr  Leu  Ser  Phe  Val  Met  Leu  Leu  Ala  Ala  Leu  Ser  Trp  Gln  Tyr
385                      390                      395                     400

Leu  Thr  Thr  Leu  Ser  Gln  Val  Thr  Glu  Asp  Tyr  Val  Gln  Thr  Gly  Glu
                    405                      410                     415

His
```

( 2 ) INFORMATION FOR SEQ ID NO:8:

( i ) SEQUENCE CHARACTERISTICS:
        ( A ) LENGTH: 444 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

```
Met  Gly  Lys  Leu  Leu  Gln  Leu  Ala  Leu  His  Pro  Val  Glu  Met  Lys  Ala
1                    5                        10                       15

Ala  Leu  Lys  Leu  Lys  Phe  Cys  Arg  Thr  Pro  Leu  Phe  Ser  Ile  Tyr  Asp
                    20                       25                  30

Gln  Ser  Thr  Ser  Pro  Tyr  Leu  Leu  His  Cys  Phe  Glu  Leu  Leu  Asn  Leu
               35                       40                  45

Thr  Ser  Arg  Ser  Phe  Ala  Ala  Val  Ile  Arg  Glu  Leu  His  Pro  Glu  Leu
     50                       55                       60

Arg  Asn  Cys  Val  Thr  Leu  Phe  Tyr  Leu  Ile  Leu  Arg  Ala  Leu  Asp  Thr
65                       70                       75                       80

Ile  Glu  Asp  Asp  Met  Ser  Ile  Glu  His  Asp  Leu  Lys  Ile  Asp  Leu  Leu
               85                       90                       95

Arg  His  Phe  His  Glu  Lys  Leu  Leu  Leu  Thr  Lys  Trp  Ser  Phe  Asp  Gly
               100                      105                      110

Asn  Ala  Pro  Asp  Val  Lys  Asp  Arg  Ala  Val  Leu  Thr  Asp  Phe  Glu  Ser
          115                      120                      125

Ile  Leu  Ile  Glu  Phe  His  Lys  Leu  Lys  Pro  Glu  Tyr  Gln  Glu  Val  Ile
     130                      135                      140

Lys  Glu  Ile  Thr  Glu  Lys  Met  Gly  Asn  Gly  Met  Ala  Asp  Tyr  Ile  Leu
145                      150                      155                      160

Asp  Glu  Asn  Tyr  Asn  Leu  Asn  Gly  Leu  Gln  Thr  Val  His  Asp  Tyr  Lys
                    165                      170                      175

Val  Tyr  Cys  His  Tyr  Val  Ala  Gly  Leu  Val  Gly  Asp  Gly  Leu  Ile  Arg
               180                      185                      190

Leu  Ile  Val  Ile  Ala  Lys  Phe  Ala  Asn  Glu  Ser  Leu  Tyr  Ser  Asn  Glu
          195                      200                      205

Gln  Leu  Tyr  Glu  Ser  Met  Gly  Leu  Phe  Leu  Gln  Lys  Thr  Asn  Ile  Ile
     210                      215                      220

Arg  Asp  Tyr  Asn  Glu  Asp  Leu  Val  Asp  Gly  Arg  Ser  Phe  Trp  Pro  Lys
225                      230                      235                      240

Glu  Ile  Trp  Ser  Gln  Tyr  Ala  Pro  Gln  Leu  Lys  Asp  Phe  Met  Lys  Pro
                    245                      250                      255

Glu  Asn  Glu  Gln  Leu  Gly  Leu  Asp  Cys  Ile  Asn  His  Leu  Val  Ile  Asn
               260                      265                      270

Ala  Leu  Ser  His  Val  Ile  Asp  Val  Leu  Thr  Tyr  Leu  Ala  Ser  Ile  His
          275                      280                      285

Glu  Gln  Ser  Thr  Phe  Gln  Phe  Cys  Ala  Ile  Pro  Gln  Val  Met  Ala  Ile
     290                      295                      300
```

| Ala | Thr | Leu | Ala | Leu | Val | Phe | Asn | Asn | Arg | Glu | Val | Leu | His | Gly | Asn |
| 305 | | | | 310 | | | | | 315 | | | | | | 320 |

| Val | Lys | Ile | Arg | Lys | Gly | Thr | Thr | Cys | Tyr | Leu | Ile | Leu | Lys | Ser | Arg |
| | | | 325 | | | | | 330 | | | | | | 335 | |

| Thr | Leu | Arg | Gly | Cys | Val | Glu | Ile | Phe | Asp | Tyr | Tyr | Leu | Arg | Asp | Ile |
| | | | 340 | | | | | 345 | | | | | 350 | | |

| Lys | Ser | Lys | Leu | Ala | Val | Gln | Asp | Pro | Asn | Phe | Leu | Lys | Leu | Asn | Ile |
| | | 355 | | | | | 360 | | | | | 365 | | | |

| Gln | Ile | Ser | Lys | Ile | Glu | Gln | Phe | Met | Glu | Glu | Met | Tyr | Gln | Asp | Lys |
| | | 370 | | | | | 375 | | | | | 380 | | | |

| Leu | Pro | Pro | Asn | Val | Lys | Pro | Asn | Glu | Thr | Pro | Ile | Phe | Leu | Lys | Val |
| 385 | | | | | 390 | | | | | 395 | | | | | 400 |

| Lys | Glu | Arg | Ser | Arg | Tyr | Asp | Asp | Glu | Leu | Val | Pro | Thr | Gln | Gln | Glu |
| | | | | 405 | | | | | 410 | | | | | 415 | |

| Glu | Glu | Tyr | Lys | Phe | Asn | Met | Val | Leu | Ser | Ile | Ile | Leu | Ser | Val | Leu |
| | | | 420 | | | | | 425 | | | | | 430 | | |

| Leu | Gly | Phe | Tyr | Tyr | Ile | Tyr | Thr | Leu | His | Arg | Ala |
| | | 435 | | | | | 440 | | | | |

(2) INFORMATION FOR SEQ ID NO:9:

(i) SEQUENCE CHARACTERISTICS:
        (A) LENGTH: 460 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:9:

| Met | Ser | Leu | Ala | Asn | Arg | Ile | Glu | Glu | Ile | Arg | Cys | Leu | Cys | Gln | Tyr |
| 1 | | | | 5 | | | | | 10 | | | | | 15 | |

| Lys | Leu | Trp | Asn | Asp | Leu | Pro | Ser | Tyr | Gly | Glu | Asp | Glu | Asn | Val | Pro |
| | | | 20 | | | | | 25 | | | | | 30 | | |

| Gln | Asn | Ile | Arg | Arg | Cys | Tyr | Gln | Leu | Leu | Asp | Met | Thr | Ser | Arg | Ser |
| | | | 35 | | | | | 40 | | | | | 45 | | |

| Phe | Ala | Val | Val | Ile | Lys | Gln | Leu | Pro | Asn | Gly | Ile | Arg | Gln | Ala | Val |
| | 50 | | | | | 55 | | | | | 60 | | | | |

| Met | Ile | Phe | Tyr | Leu | Val | Leu | Arg | Gly | Leu | Asp | Thr | Val | Glu | Asp | Asp |
| 65 | | | | | 70 | | | | | 75 | | | | | 80 |

| Met | Thr | Leu | Pro | Leu | Asp | Lys | Lys | Leu | Pro | Ile | Leu | Arg | Asp | Phe | Tyr |
| | | | | 85 | | | | | 90 | | | | | 95 | |

| Lys | Thr | Ile | Glu | Val | Glu | Gly | Trp | Thr | Phe | Asn | Glu | Ser | Gly | Pro | Asn |
| | | | 100 | | | | | 105 | | | | | 110 | | |

| Glu | Lys | Asp | Arg | Gln | Leu | Leu | Val | Glu | Phe | Asp | Val | Val | Ile | Lys | Glu |
| | | | 115 | | | | | 120 | | | | | 125 | | |

| Tyr | Leu | Asn | Leu | Ser | Glu | Gly | Tyr | Arg | Asn | Val | Ile | Ser | Asn | Ile | Thr |
| | 130 | | | | | 135 | | | | | 140 | | | | |

| Lys | Glu | Met | Gly | Asp | Gly | Met | Ala | Tyr | Tyr | Ala | Ser | Leu | Ala | Glu | Lys |
| 145 | | | | | 150 | | | | | 155 | | | | | 160 |

| Asn | Asp | Gly | Phe | Ser | Val | Glu | Thr | Ile | Glu | Asp | Phe | Asn | Lys | Tyr | Cys |
| | | | | 165 | | | | | 170 | | | | | 175 | |

| His | Tyr | Val | Ala | Gly | Leu | Val | Gly | Ile | Gly | Leu | Ser | Arg | Leu | Phe | Ala |
| | | | 180 | | | | | 185 | | | | | 190 | | |

| Gln | Ser | Lys | Leu | Glu | Asp | Pro | Asp | Leu | Ala | His | Ser | Gln | Ala | Ile | Ser |
| | | | 195 | | | | | 200 | | | | | 205 | | |

| Asn | Ser | Leu | Gly | Leu | Phe | Leu | Gln | Lys | Val | Asn | Ile | Ile | Arg | Asp | Tyr |

```
         210                           215                              220
Arg  Glu  Asp  Phe  Asp  Asn  Arg  His  Phe  Trp  Pro  Arg  Glu  Ile  Trp
225                      230                    235                      240

Ser  Lys  Tyr  Thr  Ser  Ser  Phe  Gly  Asp  Leu  Cys  Ile  Pro  Cys  Asn  Ser
                    245                      250                      255

Glu  Lys  Ala  Leu  Glu  Cys  Leu  Ser  Asp  Met  Thr  Ala  Asn  Ala  Leu  Thr
                    260                      265                      270

His  Ala  Thr  Asp  Ala  Leu  Val  Tyr  Leu  Ser  Gln  Leu  Lys  Thr  Gln  Glu
          275                           280                     285

Ile  Phe  Asn  Phe  Cys  Ala  Ile  Pro  Gln  Val  Met  Ala  Ile  Ala  Thr  Leu
     290                      295                     300

Ala  Ala  Val  Phe  Arg  Asn  Pro  Leu  Val  Phe  Gln  Thr  Asn  Val  Lys  Ile
305                      310                     315                      320

Arg  Lys  Gly  Gln  Ala  Val  Gln  Ile  Ile  Leu  His  Ser  Val  Asn  Leu  Lys
                    325                      330                      335

Asn  Val  Cys  Asp  Leu  Phe  Leu  Arg  Tyr  Thr  Arg  Asp  Ile  His  Tyr  Lys
               340                      345                      350

Asn  Thr  Pro  Lys  Asp  Pro  Asn  Phe  Leu  Lys  Ile  Ser  Ile  Glu  Cys  Gly
          355                      360                      365

Lys  Ile  Glu  Gln  Val  Ser  Glu  Ser  Leu  Phe  Pro  Arg  Arg  Phe  Arg  Glu
     370                      375                      380

Met  Tyr  Glu  Lys  Ala  Tyr  Val  Ser  Lys  Leu  Ser  Glu  Gln  Lys  Lys  Gly
385                      390                      395                      400

Asn  Gly  Thr  Gln  Lys  Ala  Ile  Leu  Asn  Asp  Glu  Gln  Lys  Glu  Leu  Tyr
                    405                      410                      415

Arg  Lys  Asp  Leu  Gln  Lys  Leu  Gly  Ile  Ser  Ile  Leu  Phe  Val  Phe  Phe
               420                      425                      430

Ile  Ile  Leu  Val  Cys  Leu  Ala  Val  Ile  Phe  Tyr  Val  Phe  Asn  Ile  Arg
          435                      440                      445

Ile  His  Trp  Ser  Asp  Phe  Lys  Glu  Leu  Asn  Leu  Phe
     450                      455                    460
```

(2) INFORMATION FOR SEQ ID NO:10:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Tyr  Asp  Asp  Glu  Leu  Val  Pro  Thr  Gln  Gln  Glu  Glu  Glu  Tyr
1                   5                        10
```

(2) INFORMATION FOR SEQ ID NO:11:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GCAGATCTCA CACAATGGGA AAGCTATTAC AATT    34

(2) INFORMATION FOR SEQ ID NO:12:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

GTCTAGATCT TGTACTCTTC TTCTTGTTGG GTTG      34

( 2 ) INFORMATION FOR SEQ ID NO:13:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:13:

GATCCGTATT GAAGGTCGAC T      21

( 2 ) INFORMATION FOR SEQ ID NO:14:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:14:

GGTCTAGAGT CTGCGCCAAA TAACATAAAC AAAC      34

( 2 ) INFORMATION FOR SEQ ID NO:15:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:15:

GTCTAGATCT AGAGTTGCCT AAGACTTTGC GTCG      34

( 2 ) INFORMATION FOR SEQ ID NO:16:

( i ) SEQUENCE CHARACTERISTICS:
    ( A ) LENGTH: 33 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:16:

GGAGTAYTGY CAYTAYGTNG CNGGNCTNGT NGG      33

( 2 ) INFORMATION FOR SEQ ID NO:17:

( i ) SEQUENCE CHARACTERISTICS:
    ( A ) LENGTH: 35 base pairs
    ( B ) TYPE: nucleic acid
    ( C ) STRANDEDNESS: single (D) TOPOLOGY: linear (ii) MOLECULE TYPE: cDNA (xi) SEQUENCE DESCRIPTION: SEQ ID NO:17:

GGATGCATNG CCATNACYTG NGGNATNGCR CARAA 35

(2) INFORMATION FOR SEQ ID NO:18:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:18:

CCAATGGCGA AGAAGTCCAA AGCTT 25

(2) INFORMATION FOR SEQ ID NO:19:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:19:

GCGGTCGACC GCCAGTCTGG TTGGTAAAGG AAAGAGTG 38